United States Patent [19]

Sasaki

[11] Patent Number: 5,575,809
[45] Date of Patent: Nov. 19, 1996

[54] ELECTRICAL STIMULATOR

[75] Inventor: Minoru Sasaki, Yokohama, Japan

[73] Assignee: Kabushiki Kaisya Advance, Tokyo, Japan

[21] Appl. No.: 75,399

[22] Filed: Jun. 11, 1993

[30] Foreign Application Priority Data

| Jun. 12, 1992 | [JP] | Japan | 4-177782 |
| Jun. 12, 1992 | [JP] | Japan | 4-177783 |
| Jun. 12, 1992 | [JP] | Japan | 4-177784 |
| Jun. 12, 1992 | [JP] | Japan | 4-177785 |
| Jun. 12, 1992 | [JP] | Japan | 4-177786 |
| Jun. 12, 1992 | [JP] | Japan | 4-177787 |
| Jun. 12, 1992 | [JP] | Japan | 4-177788 |
| Jun. 12, 1992 | [JP] | Japan | 4-177790 |

[51] Int. Cl.$^6$ .................................................. A61N 1/36
[52] U.S. Cl. .................................................. 607/62
[58] Field of Search .................. 607/62, 72, 22, 607/24, 25, 44; 600/26; 128/687, 905

[56] References Cited

U.S. PATENT DOCUMENTS

| 2,368,207 | 1/1945 | Eaton | 607/62 |
| 3,650,277 | 3/1972 | Sjostrand et al. | 607/44 |
| 4,399,821 | 8/1983 | Bowers | 607/72 |
| 4,535,777 | 8/1985 | Castel | 128/421 |
| 4,733,667 | 3/1988 | Olive et al. | 607/24 |

FOREIGN PATENT DOCUMENTS

| 3314128 | 10/1984 | Germany | 607/44 |
| 91099706 | 12/1992 | Germany . | |
| 51-116076 | 10/1976 | Japan . | |
| 55-99262 | 7/1980 | Japan . | |
| 82104425 | 6/1993 | Taiwan . | |
| WO84/03219 | 8/1984 | WIPO . | |
| WO90/04955 | 5/1990 | WIPO . | |

OTHER PUBLICATIONS

Oximeters, Pulse, HPCS, Feb., 1993.
Electrical Stimulation for Muscle Strengthening, Liao et al., Mar., 1991.

Primary Examiner—William E. Kamm
Attorney, Agent, or Firm—Finnegan, Henderson, Farabow, Garrett and Dunner, L.L.P.

[57] ABSTRACT

An object of the present invention is to precisely lock the output of electrical stimulation pulses onto diastolic periods. An electrical stimulator comprises a pulse sensor, a systolic period pulse producing unit for producing a systolic signal using the pulse wave sensor, a signal oscillator for electrical stimulation production, an electrical stimulation pulse output unit for outputting electrical stimulation pulses according to the output signal of the signal oscillator for electrical stimulation production, and a gate for controlling the connection between the signal oscillator for electrical stimulation production and the electrical stimulation pulse output unit according to the systolic signal supplied by the systolic period signal producing unit.

2 Claims, 22 Drawing Sheets

X DIASTOLIC PERIOD

N    A

ELECTRICAL STIMULATOR

BACKGROUND OF THE INVENTION

1. Field of the Invention

The present invention relates to an electrical stimulator.

2. Description of the Related Art

A biomedical signal such as a series of pulses is used to detect periods during which it is preferred to stimulate a living body. Electrical stimulation is then applied to the living body mainly during these periods. This method is very effective in improving blood circulation and is not comparable with a conventional electrical stimulator, for example, a low-frequency treatment apparatus.

What are referred to as "periods during which it is preferred to apply stimulation to a living body" are periods (diastolic periods) in the activity of the heart during which blood returns to the heart via the veins. In general, the veins have no source of a force for driving blood. If a supplementary power for driving blood is applied to the veins, the blood circulation is immediately improved.

To be more specific, a biomedical signal such as an electrocardiogram is used to detect diastolic periods. Stimulation is then applied mainly during the diastolic periods. This modality accelerates blood circulation very efficiently, which is not comparable with a conventional electrical massager, low-frequency treatment device, or other electrical stimulator. Moreover, acceleration of blood circulation results in weight reduction.

When an attempt is made to constitute the foregoing apparatus, the apparatus comprises, for example, a means for detecting a heart-beat signal, a means for discriminating a diastolic signal from the heart-beat wave, and an output means for outputting electrical stimulation pulses in response to the input of the diastolic signal.

In the output means for outputting electrical stimulation pulses in response to the input of a diastolic signal, when the means is materialized in practice, some problems arise. That is to say, an initial transient delay due to component parts occurs before the output of electric stimulation pulses. When a microcomputer is employed, a program routine for preventing an erroneous operation caused by noises is installed. Consequently, the output of electrical stimulation pulses is not completely locked onto a diastolic signal. For constituting a portable apparatus, the number of parts must be minimized. Any other device can therefore not be incorporated.

In the aforesaid apparatus, it is very important to detect diastolic periods.

In a method offering a means for detecting diastolic period, systolic periods are detected first, and then reversed or removed. A systolic period refers, for example, as indicated with SS in FIG. 1, to a period from the a minimum value to a peak value. The lowest value indicating the start of a systolic period is not detected accurately in practice or hardly detected due to artifacts or depending on a region in which a biomedical signal is detected.

Unlike a pulse monitor, the apparatus must detect not only pulses but also output and stop electrical stimulation pulses. Moreover, a means that can be operated more easily and reliably is required to detect systolic periods or diastolic periods.

On the other hand, a pulse wave varies depending on the activity of the heart. Violent exercises or psychological excitation results in smaller pulse durations and narrower diastolic periods.

In this state, even if electrical stimulation is applied during diastolic periods, only a limited effect is expected. Moreover, electrical stimulation may not be locked onto the diastolic periods. On the contrary, electrical stimulation may be applied during (systolic) periods during which the heart feeds blood, which degrades the force of feeding blood. An extra load is imposed on the heart. In this kind of electrical stimulator, which is preferred to be used for a prolonged period of time continuously, a means for copying with narrowing pulse durations of a pulse wave has been in need.

SUMMARY OF THE INVENTION

According to the first aspect of the present invention, an electrical stimulator includes an oscillating means for oscillating electrical stimulation drive pulses, and a gate means for controlling the on or off operation of the connection between the oscillating means and a driver that outputs stimulation pulses, which have been boosted with drive pulses oscillated by the drive pulse oscillating means, or electrical stimulation pulses which have been boosted and stored to be responsive to a living body. A systolic signal derived from a pulse wave is input to an input port for breaking or making the gate, thus turning off the gate means during input. Eventually, the output of electrical stimulation pulses is locked onto diastolic periods.

According to the second aspect of the present invention, an electrical stimulator comprises a pulse sensor, a means for differentiating a pulse signal provided by the pulse wave sensor, and a peak hold means for holding every peak potential of a differential wave provided by the differentiating means and decreasing each held peak potential for a specified time constant. The output differential wave of the differentiating means is compared with the output potential of the peak hold means. When the differential wave exceeds the peak hold potential, a pulse is allowed to rise or fall. At the time of the rise or fall, the pulse signal assumes a minimum value; that is, a systolic period starts. When electrical stimulation is stopped at least at the start of each systolic period, electrical stimulation can be applied reliably during diastolic periods. The start of electrical stimulation is determined as a point at which an arbitrary period of time has passed since the start of a systolic period, which may be determined using any other means. Herein, "electrical stimulation is stopped at least at the start of each systolic period" means that electrical stimulation may be stopped at any other points. Specifically, electrical stimulation is controlled at the start of a systolic period so that an interval of electrical stimulation will be as long as an arbitrary period of time.

According to the third aspect of the present invention, when an pulse duration of a pulse wave becomes narrower than a specified value, stimulation during every diastolic period is ceased. Electrical stimulation is provided during every other or multiple diastolic periods. This results in an electrical stimulator that imposes no load on the activity of the heart, is preferred for a prolonged use, and permits sedation of the activity of the heart.

BRIEF DESCRIPTION OF THE DRAWINGS

FIGS. 7a to 7f waves detected in the components of an example relating to the second aspect of the present invention having the circuitry in FIG. 5;

DESCRIPTION OF THE PREFERRED EMBODIMENT

Figure 2:
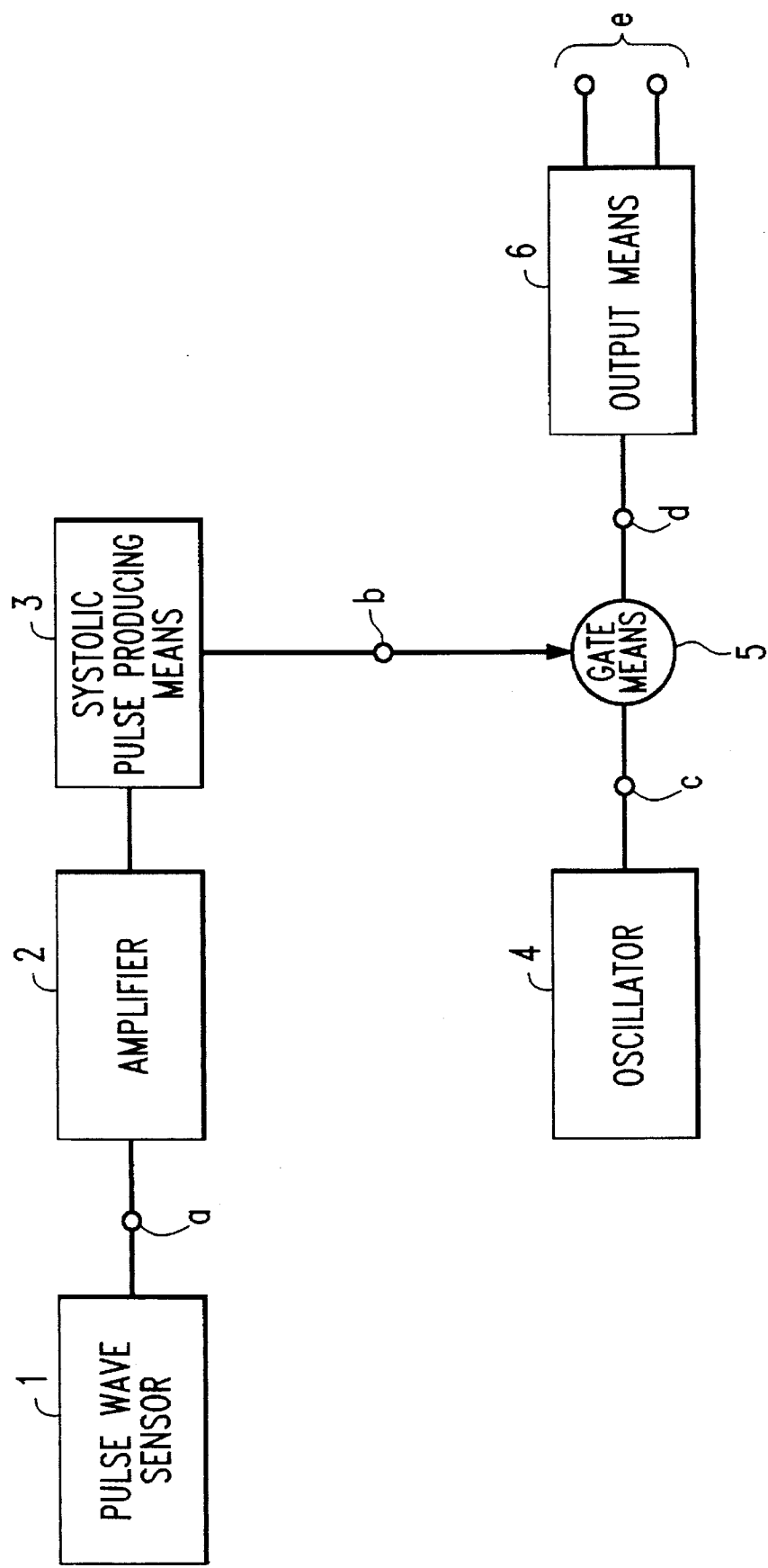
FIG. 2 is a block diagram of an example relating to the first aspect of the present invention.

FIG. 2 is a block diagram showing an embodiment relating to the first aspect of the present invention.

1 denotes a pulse wave sensor comprising, for example, a photoelectric transducer or a piezoelectric transducer. The pulse wave sensor 1 is put on an earlobe, a fingertip, or the like.

An alternative means uses electrodes to directly catch an electric signal originating from any region of a living body.

2 denotes an amplifier or a means for amplifying current or voltage.

3 denotes a systolic pulse producing means for detecting systolic periods in a pulse wave signal and outputting pulses representing the systolic periods. The method of detection varies widely but is not limited to any specific one.

4 denotes an oscillator for outputting homopolarity pulses. The oscillator 4 is controlled to provide a constant or variable pulse width or duration. A main component is a multivibrator.

5 denotes a gate circuit consisting mainly of an AND gate, OR gate, NAND gate, and NOR gate.

6 denotes an output means comprising a boosting element such as a transformer or a coil, a switching element such as a switching transistor or an FET, and a storage element such as a capacitor. The exciting current of the boosting element is cut off by breaking the switching element, thus outputting pulses of up to 200 volts. Alternatively, the exciting current of the boosting element is intermittently ON and OFF at a vote of several kilohertz, so that boosted pulses each voltage of which is unresponsive to a living body are generated. The output pulses do not stimulate the human body. These boosted pulses are stored in the storage element until an accumulated voltage in the storage element can stimulate a living body.

The output terminal of the pulse wave sensor 1 is connected to the amplifier 2 via terminal a. The output terminal of the amplifier 2 is connected to the systolic pulse producing means 3. The input terminal of the systolic pulse producing means 3 is connected to a control input port of the gate means 5 via a terminal b.

The output terminal of the oscillator 4 is input to the input port of the gate means 5 via a terminal C, and the output port of the gate means 5 is connected to the output means 6 via a terminal d.

The output terminal of the output means 6 is connected to a pair of terminals e. The pair of terminals e are coupled with conductors.

Figure 3A:
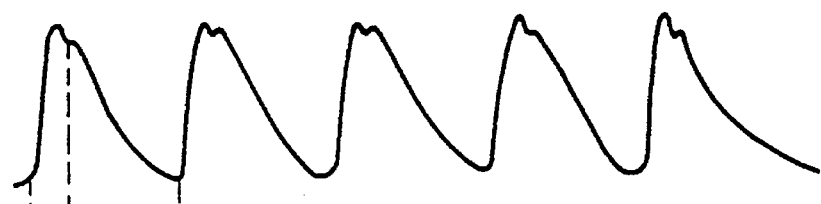
FIGS. 3a to 3d show waves detected in the components shown in FIG. 2.
Figure 3B:
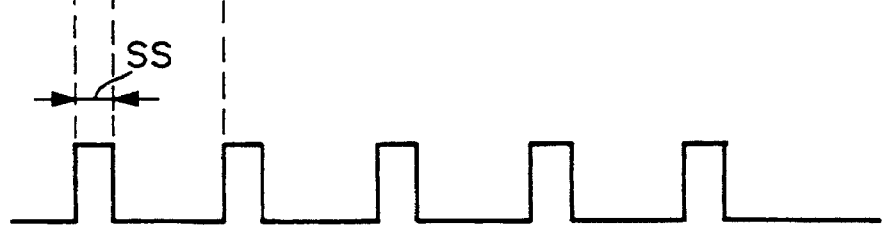

Next, the operations of FIG. 2 will be described in detail with reference to FIG. 3a to 3d. The pulse wave sensor 1 converts a pulse wave originating from a living body into an electric signal, and outputs a wave shown in FIG. 3a via the terminal a. The amplifier 2 amplifies the electric signal. The systolic pulse producing means 3 decodes the electric signal into systolic pulses SS and outputs the systolic pulses SS via a terminal. FIG. 3b shows the systolic pulses. The oscillator 4 outputs pulses shown in FIG. 3c via the terminal c. The gate means 5 disconnects the output via the terminal c according to the systolic pulse, and outputs pulses shown in FIG. 3d. The output means 6 produces boosted pulses in response to the pulses shown in FIG. 3d, and outputs boosted pulses via the terminal e.

From the viewpoint of practicability, such a system will not ensure that the gate means for extending control in response mainly to systolic pulses output by the systolic pulse producing means will never apply electrical stimulation pulses to a human body during systolic periods.

Specifically, since violent exercise raises the pulse rate, periods of a pulse wave during which electrical stimulation pulses can be applied become very short and the application of stimulation pulses becomes meaningless. When a pulse rate gets high, it is more effective to repeat a sequence that the gate means is turned off during systolic periods so that no electrical stimulation pulse will be generated in response to an initial pulse wave, and then the gate means holds in an ON condition during periods including systolic periods for the subsequent pulse wave.

An electrical stimulator of the present invention is often used continuously for a prolonged period of at leans 30 min.

to 8 hours. For a short use, even when electrical stimulation pulses are applied during systolic periods, the advantages of the stimulator do not differ greatly from those when no electrical stimulation pulses are applied during systolic periods. In other words, what counts most is that stimulation applied to a human body during the entirety of the diastolic periods should be apparently higher in density. A duration of an electrical stimulation pulse may be either long or short, or may be applied either continuously or intermittently. Electrical stimulation pulses sensitive to a human body have pulse widths of several hundreds of microseconds. The pulse widths is, however, as large as several hundreds of milliseconds during diastolic periods. Multiple consecutive electrical stimulation pulses may sometimes be output with different amplitudes.

A technique of outputting electrical stimulation pulses is not limited to any specific technique. In a preferable technique, boosted pulses having frequencies, ranging from several kilohertz to several tens of kilohertz are generated, stored in a storage means until the accumulated voltage thereat becomes a voltage detectable by a human body and then discharged. This technique is also helpful in saving energy and in changing operating modes.

Figure 4:
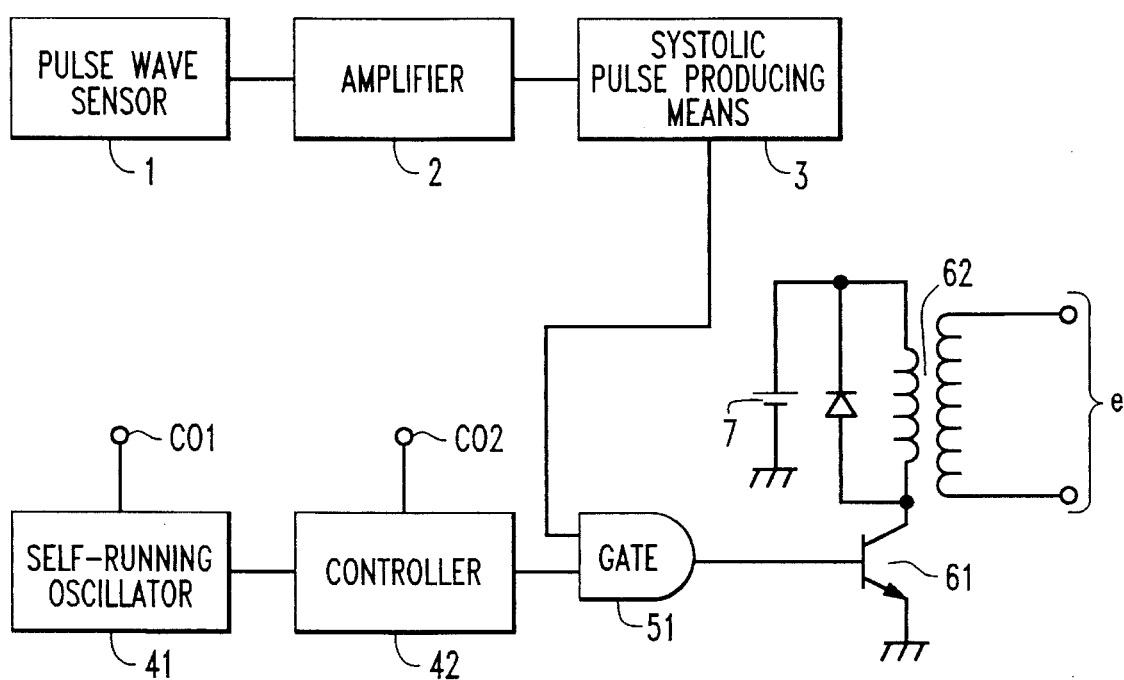
FIG. 4 is a block diagram of another example relating to the first aspect of the present invention.

FIG. 4 shows another embodiment according to the first aspect of the present invention.

Figure 1:
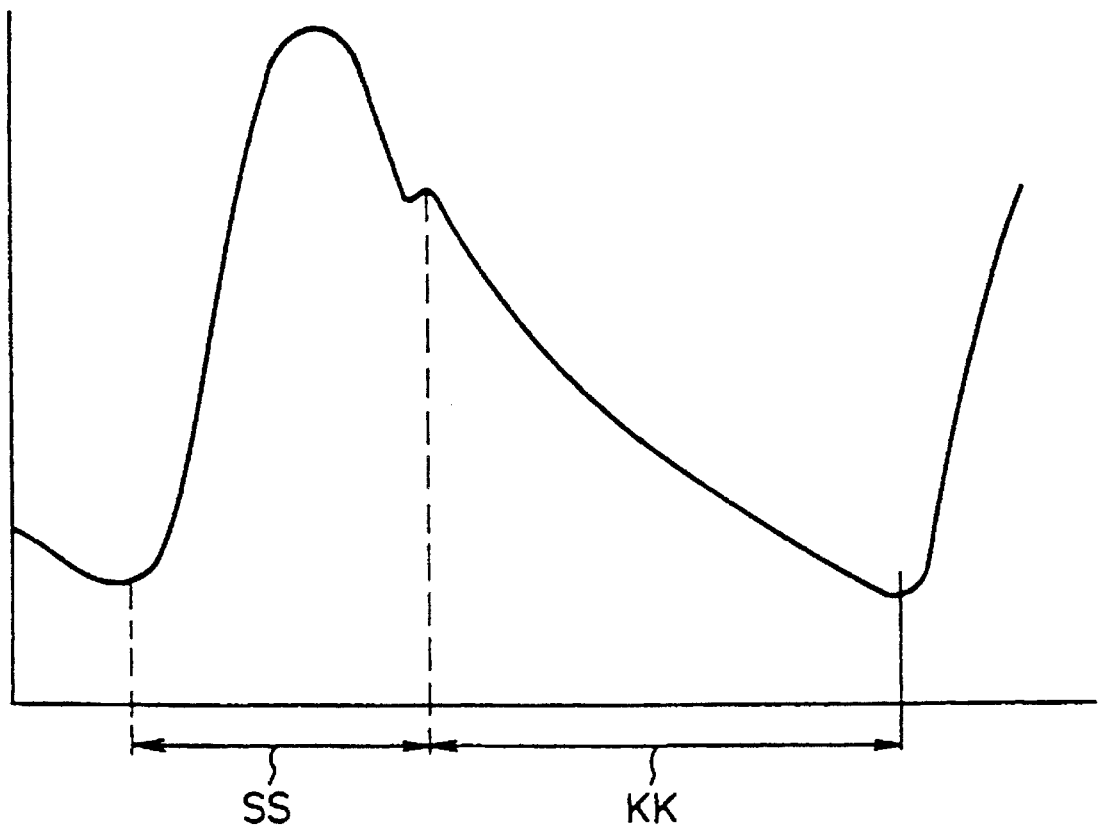
FIG. 1 shows an example of a pulse wave detected in the present invention.

The pulse wave sensor 1, amplifier 2, and systolic pulse producing means 3 have the same configurations as those shown in FIG. 1. The description will therefore be omitted.

The output of the systolic pulse producing means 3 is driven low during systolic periods, and high during other periods.

In short, the output of the systolic pulse generating means 3 shown in FIG. 2 is reversed in polarity.

In an electric stimulator relating to the present invention, efforts have been made to detect the systolic periods SS and diastolic periods KK as those shown in FIG. 1 in a pulse wave as precisely as possible. No electrical stimulation pulses are applied during systolic periods SS, and electrical stimulation pulses are applied only during diastolic periods KK.

As apparent from FIGS. 3a to 3d, the systolic pulse producing means 3 outputs systolic pulses as those shown in FIG. 3b during periods corresponding to systolic periods detected by the pulse wave sensor 1. On the other hand, the oscillator 4 that oscillates at a specified frequency generates uniform pulses, as those shown in FIG. 3c, each having a certain cycle, and inputs the pulses to the gate means 5.

Figure 3C:
Figure 3D:
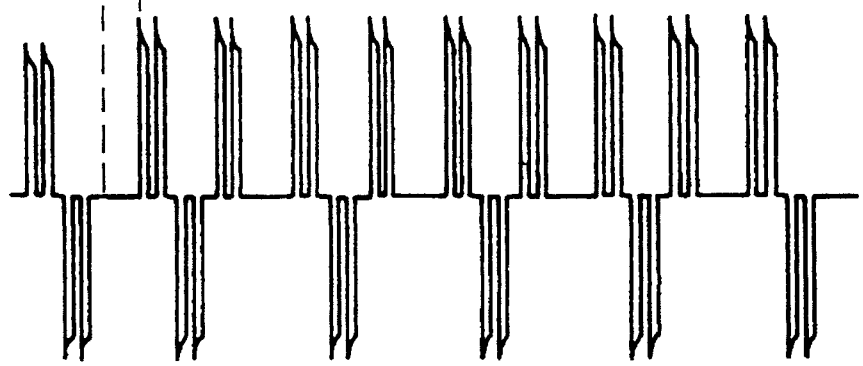

The gate means 5 then receives the input pulses forming the wave as shown in FIG. 3c and the systolic pulses forming the wave as shown in FIG. 3b and generates electrical stimulation pulses shown in FIG. 3d.

In this example, no electrical stimulation pulses are generated during periods corresponding to the systolic periods SS in a pulse wave, so that no electrical stimulation pulses will be applied to a living body.

According to the first aspect of the present invention, no electrical stimulation pulses may be generated during systolic periods SS. Alternatively, a certain number of electrical stimulation pulses may be generated during the systolic periods SS.

In the example according to the first aspect of the present invention, the polarities of electrical stimulation pulses as shown in 3d should preferably be reversed from time to time. Reversing the polarities of electrical stimulation pulses facilitates depolarization of a living body receiving the electrical stimulation pulses.

41 denotes a self-running oscillator that is, for example, a self-running multivibrator. The frequency duty ratio is modified according to an input received via a control input terminal CO1.

42 denotes a controller that is, for example, a monostable multivibrator. The controller 42 outputs pulses each having a duty ratio that has been modified according to an input received via a control input terminal CO2.

51 denotes a gate that comprises an AND gate.

61 denotes a driver that is a switching element. In this embodiment, a transistor is employed.

62 denotes a boosting means that is a transformer, a coil, a chopper type boosting circuit, a single-turn coil, or the like. In this embodiment, a transformer is employed. In the transformer, the ratio of the number of turns of its primary and secondary windings may be the same or different from each other.

7 denotes a battery that comprises one or multiple primary or secondary batteries.

The output terminal of the systolic pulse producing means 3 is connected to one terminal of the gate 51. An output of the self-running oscillator 41 is fed to the other terminal of the gate 51 via the controller 42. An output of the gate 51 is fed to the base of the transistor 61. The collector output of the transistor 61 is fed to one primary terminal of the transformer 62. The other primary terminal of the transformer 62 is connected to a plus electrode of the battery 7. The secondary terminals of the transformer are connected to the output terminals e and coupled with conductors.

Next, the operations will be described.

The oscillator 41 outputs pulses whose frequencies and duty ratios have been set according to an input signal passing through the control input terminal CO1. The pulses are fed to the controller 42, and supplied after having the duty ratios controlled according to an input signal passing through the control input terminal CO2. The pulses provided by the controller 42 are input to the gate means 51. When the systolic pulse producing means 3 outputs high-level pulses, the pulses output by the controller 42 are supplied via the gate means 51. When the pulses are input to the gate means 51 with the levels held low, the output pulses of the gate means 51 are held low.

The pulses provided by the gate means 51 are input as drive pulses to the transistor 61. The transistor 61 performs breaking. The breaking done by the transistor 61 cuts off the exciting current flowing through the primary winding of the transformer 62. When the exciting current is cut off in the primary winding, the secondary winding outputs a resultant back electromotive force via the output terminals e. The back electromotive force reaches 100 volts and has a range exceeding a threshold responsive to a human body, which provides stimulation pulses. In this case, however, a load to the battery 7 increases. Moreover, it takes some time to store electric energy in the coil or transformer. These features may not be preferable for a continuous use for six to seven hours, or for production of electrical stimulation pulses in various modes.

Next, an example according to the second aspect of the present invention will be described with reference to FIG. 5.

In this example according to the second aspect, a one-chip microcomputer is engaged in major control for an electrical stimulator.

The operations of a microcomputer 35 in this example is based on a drive pulse production program serving as a main routine. Systolic pulses are input as an interrupt signal.

During the pulse durations of the pulses, the drive pulse production program running in the microcomputer is suspended or combined with another routine program so as to set up a state in which no drive pulses are supplied to the microcomputer via the output terminal thereof.

Each of the systolic pulses input to the microcomputer 35 need not have a pulse width exactly corresponding to a systolic period. For example, a systolic pulse may merely indicate the start or end of a systolic period. With the input of this pulse, the microcomputer 35 activates a program for converting the pulse into a pulse representing a systolic period SS. During the systolic period, the drive pulse production program is suspended, and then another instruction, for example, an instruction instructing to set up the state of an output port according to the state of a driver is being executed. Alternatively, the drive pulse production program is, as mentioned above, combined with another routine program, and then no drive pulse is output via the output terminal.

The suspension caused by an interrupt is preferred for this embodiment, when the drive pulse production program is used as the main routine of the one-chip microcomputer 35.

The microcomputer 35 may be formed as a mere substitute for the systolic pulse production means 3 and gate means 5 in FIG. 1, or as a mere substitute for the systolic pulse production means 3, gate means 5, or oscillator 4.

Next, an example of a more specific configuration will be described in conjunction with FIG. 5.

31 denotes a pulse wave sensor made up of a light emitting diode (cds or LED) and a phototransistor. The pulse wave sensor 31 converts a change in light resulting from a blood flow into an electrical change, and outputs the electrical change.

32 denotes a differentiating circuit structured to serve as an amplifying means as well.

33 denotes a peak hold circuit that when receiving an input, provides an output in which the potential of the input is held. The peak hold circuit employed for the present invention preferably holds every peak potential of an input signal and decreases each peak potential within a specified time constant.

That is to say, the peak hold circuit 33 holds every peak potential, and then outputs a voltage resulting from the discharge for a specified time constant.

34 denotes a comparator that has at least two input terminals and turns on or off an output according to a potential difference between the two input terminals, which has one polarity or an opposite polarity. Herein, a potential difference of one polarity means either a positive or negative potential difference, and a potential difference of an opposite polarity means either a negative or positive potential difference. The positive or negative polarity is defined relative to the polarity of either of the inputs of the comparator 34. The comparator 34 compares the potential of a differential signal provided by the differentiating circuit 32 with that of an output signal provided by the peak hold circuit 33. When a specified potential difference occurs, the comparator 34 outputs a pulse (See FIG. 7b).

35 denotes a microcomputer that processes and checks an input signal using the data contained in a built-in memory means, and then outputs drive pulses. The drive pulses 3a, 3b, and 3c have different frequencies and duty ratios. The drive pulse 3a is used to generate a boosting pulse of several kilohertz. The drive pulses 3b and 3c have low frequencies and are used to produce electrical stimulation. The drive pulses 3b and 3c are output to change polarities. The drive pulse 3b is used for positive electrical stimulation. The drive pulse 3c is used for negative electrical stimulation.

36 denotes a switching transistor. The switching transistor 36 performs switching in response to the drive pulse 3a output by the microcomputer 35.

37 denotes a boosting inductor. The boosting inductor 37 generates a boosted pulse by cutting-off the exciting current flowing into the inductor.

38 denotes a storage means that is a capacitor.

39 denotes a switching means. 39a and 39c denote PNP switching transistors. 39b and 39d denote NPN switching transistors.

40 denotes output terminals coupled with conductors. The output terminals 40 are attached or put on a region of a living body.

Next, the operations will be described. The pulse wave sensor 31 is put on any region of a living body, which converts a pulse wave into a potential change and outputs the potential change.

The pulse wave sensor 31 is put on any region of a living body, which converts a blood flow change into a potential change. The potential change is converted into a current signal and input to the differentiating circuit 32. The blood flow signal is converted into a differential signal by the differentiating circuit 32.

The output signal of the pulse sensor 31 is input to the differentiating circuit 32. A pulse wave signal is converted into a differentiating signal by the differentiating circuit 32 and supplied to one terminals of the peak hold circuit 33 and comparator 34.

The peak hold circuit 33 outputs a potential in which the peak potential of the differential signal is held. The potential is fed to the other terminal of the comparator 34.

The comparator 34 compares the potential of the differential signal of the differentiating circuit 32 with that of an output signal of the peak hold circuit 33. When a specified potential difference occurs, the comparator 34 outputs a pulse. The pulses constitute a pulse wave pulse signal whose first periodic point is set to a peak potential. Each of the pulses rises when the pulse wave signal takes on a minimum value.

Figures 7A, 7B, 7C, 7D, 7E, 7F:
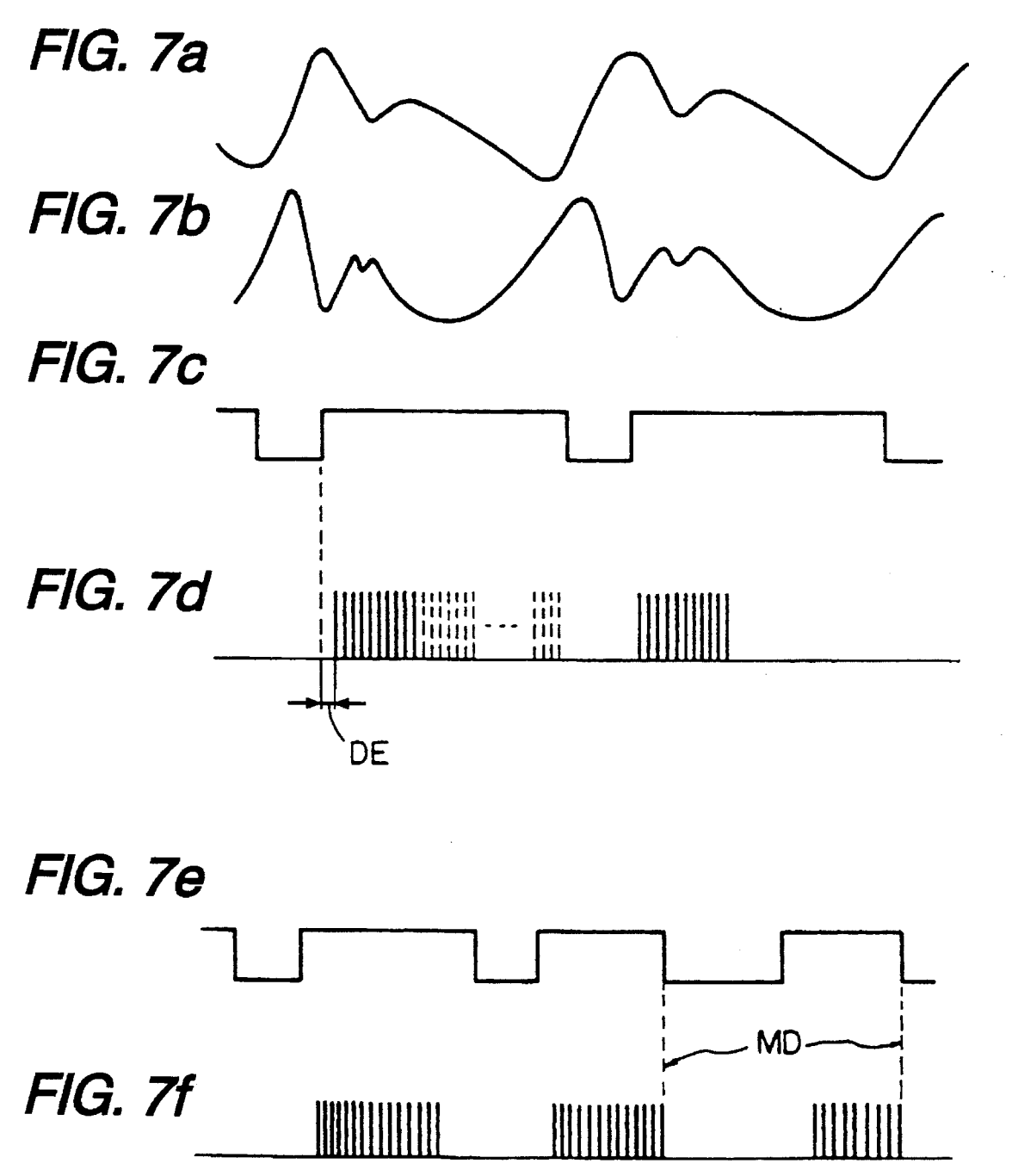

The microcomputer 35 inputs the pulse, and delays the rise of the pulse, as shown in FIG. 7d, by several microseconds to several tens of milliseconds DE. At the fall of the pulse whose rise has been delayed and which is to be input to the microcomputer 35, a delay pulse indicating a fall is produced. The pulse width of the delay pulse represents a period in which the output of electrical stimulation is permissible. The delay pulse is an imaginary pulse and works similarly to a program for setting a permissible period.

The microcomputer 35 outputs drive pulses via the terminals 3a, 3b, and 3c. The pulse supplied via the terminal 3a is a rectangular pulse having a frequency of several kilohertz. With the pulse, the transistor 36 is turned on or off. When the transistor 36 is turned on or off, the current flowing into the inductor 37 is cut off. When the current is cut off, the inductor 37 generates a back electromotive force which is then stored in the capacitor 38 via the diode.

Rectangular pulses of several hertz are output via the terminals 3b and 3c. When a pulse is output via the terminal 3b, the transistors 39b and 39c turn on and off repeatedly. Charges stored in the capacitor 38 are released via the transistor 39c, output terminal 40, load RZ, and transistor 39b. When a pulse is output via the terminal 3c, the transistors 39a and 39d turn on and off repeatedly. Charges stored in the capacitor 38 are released via the transistor 39a, output terminal 40, load RZ, and transistor 39d. Depending on whether the pulse is output via the terminal 3b or via the terminal 3c, an electrical stimulation pulse supplied via the output terminal 40 has an opposite polarity.

According to a pulse supplied by the microcomputer 35 via the terminal 3a, 3b, or 3c, electrical stimulation pulses of up to about 200 volts are supplied via the output terminal 40. The polarity of the electrical stimulation pulse varies depending on whether the original pulse is output via the terminal 3b or 3c. When the outputs provided via the terminals 3a to 3c have different pulse widths and pulse durations, varying electrical stimulation can be supplied via the output terminal 40. The varying electrical stimulation is represented as one or multiple continuous waves having pulse widths of, for example, several hundreds of microseconds, and frequencies of several tens of hertz.

On behalf of the microcomputer, a gate array or other logical circuit is usable. A program installed in the microcomputer may have any mode as long as it can perform the aforesaid operations.

Figure 6:
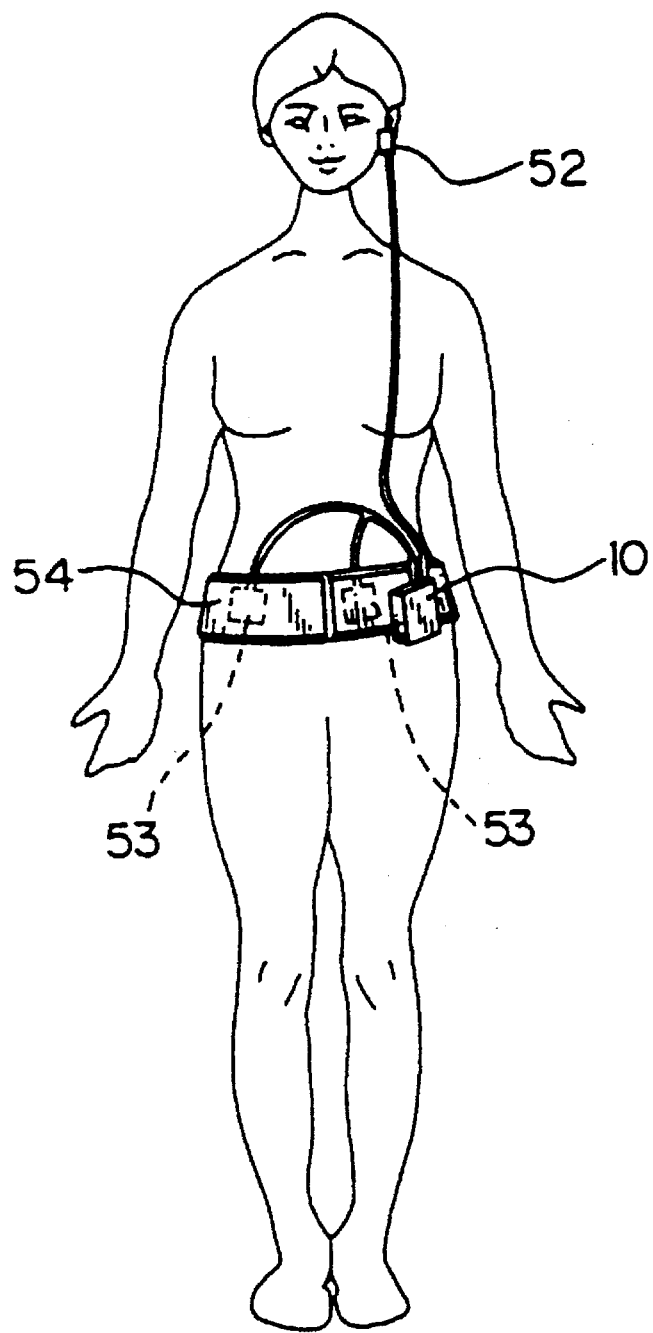
FIG. 6 shows an example of a state in which an electrical stimulator relating to the present invention is put on a human body.

FIG. 6 shows an embodiment in which the present invention is put on a human body for use. 10 denotes a main unit in which the circuits described in the previous embodiment are incorporated, and rechargeable secondary batteries are embedded. The secondary batteries are, for example, four AAA nickel-cadmium batteries. 52 denotes an ear sensor that is a photoelectric transducer type pulse wave sensor.

53 denotes conductors that are different and indifferent conductors.

The conductors 53 may be adhesive or non-adhesive as long as at least their surfaces coming into contact with a living body have conductivity.

54 denotes a belt made of cotton or synthetic fibers. The conductors 53 are clamped between the belt and abdomen, and thus immobilized.

When a use for an average of seven to eight hours a day is repeated in the above state, blood circulation is accelerated markedly. Since the muscles around the organs are moved, intracorporeal combustion of excessive fat is facilitated to realize weight reduction.

As described in detail above, according to the present invention, a pulse wave is decomposed to produce systolic pulses, a gate means cuts off the output pulses of an electrical stimulation pulse output means in response to the systolic pulses. Thus, output times of electrical stimulation pulses can be locked onto periods during which electrical stimulation pulses are applied; that is, systolic periods.

Next, the operation to be performed when the duration of a pulse wave pulse becomes shorter as shown in FIGS. 7a to 7b will be described. An electrical stimulation pulse is output for a specified time interval after a specified delay has passed since the rise of a pulse wave pulse. When a diastolic period becomes shorter than the width of an electrical stimulation pulse, if the electrical stimulation pulse is stopped forcibly at the fall (MD) of a pulse representing the start of a systolic period, the end of the electrical stimulation pulse output period agrees with the end of a diastolic period. FIG. 7f shows the operation. The operation shown in FIG. 7f is remarkable when a diastolic period becomes shorter than the pulse width of an electrical stimulation pulse. Even in a state shown in FIG. 7d, the operation is still in active.

As described above, according to the present invention, a differentiating wave is detected in a pulse wave, and converted into a peak hold voltage by a peak hold means. The peak hold voltage is then compared with the differentiating wave by a comparing means. When the differentiating wave exceeds the peak hold voltage, a pulse is allowed to rise or fall. The rise or fall agrees with the start of a systolic period. Electrical stimulation is stopped at least during all the systolic periods, which distinguishes electrical stimulation permissible periods. Consequently, electrical stimulation can be output reliably during diastolic periods.

Next, an example relating to the third aspect of the present invention will be described with reference to FIGS. 8 and 9a to 9e.

Figure 8:
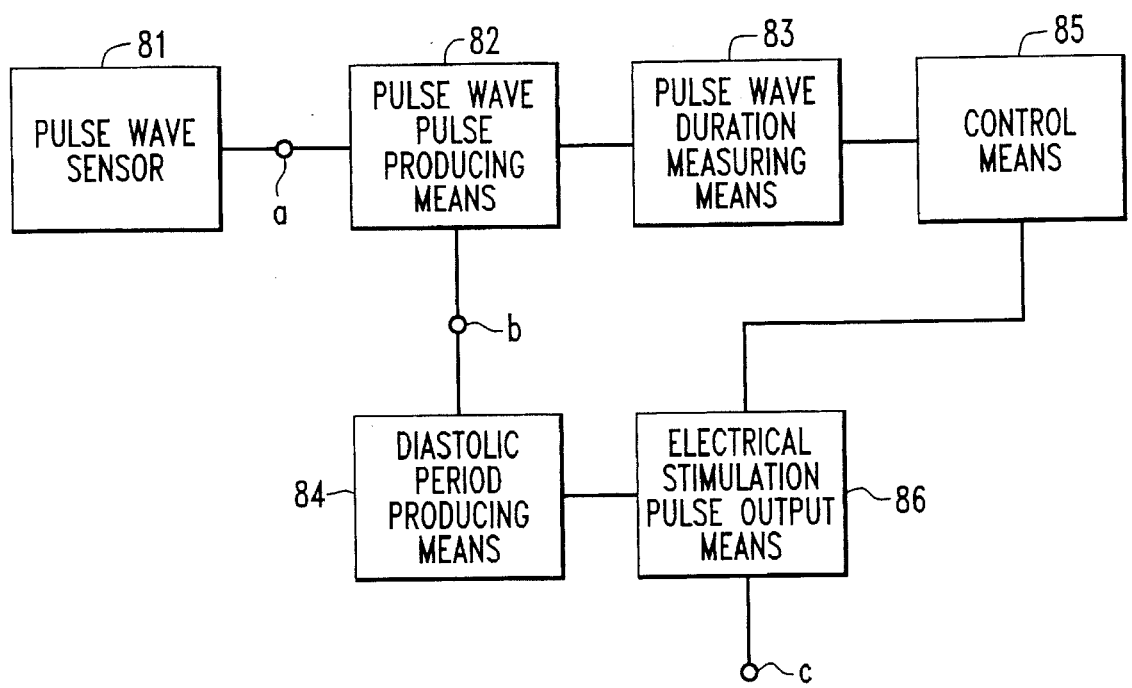
FIG. 8 is a block diagram of an example relating to the third aspect of the present invention.

FIG. 8 shows an example according to the third aspect of the present invention. FIGS. 9a to 9e shows output waves detected in the components shown in FIG. 8.

81 denotes a pulse wave sensor that is a sensor realized with, for example, a photoelectric transducer or piezoelectric transducer. The pulse wave sensor 81 is put on an earlobe, a fingertip, or an arm, and converts a pulse wave into an electric signal.

82 denotes a pulse wave pulse producing means that is a means for producing pulse wave pulses using the pulse wave electric signal. The pulse wave pulse producing means 82 detects every peak potential and bottom potential of a pulse wave, and produces pulses each of which rises with a peak potential and falls with a bottom potential, or vice versa.

83 denotes a pulse wave duration measuring means that is a means for measuring and outputting a value of a pulse duration of an output pulse of the pulse wave pulse producing means.

84 denotes a diastolic period producing means that calculates and detects a diastolic period using the output of the pulse wave pulse producing means.

85 denotes a control means. The control means 85 always monitors a duration value provided by the pulse wave duration measuring means, and outputs a control signal when the duration value becomes lower than a specified value. The "specified value" is a predetermined value or a value set according to the state.

86 is an electrical stimulation pulse output means that outputs electrical stimulation pulses according to the output signals of the diastolic period producing means 84 and the control means 85.

The pulse wave sensor 81 is connected to the pulse wave pulse producing means 82 via a terminal a. The pulse wave pulse producing means 82 is connected to the pulse wave duration measuring means 83 and diastolic period producing means 84 via a terminal b. The pulse wave duration measuring means 83 is connected to the control means 85. The diastolic period producing means 84 and control means 85 are connected to the electrical stimulation pulse output means 86. The electrical stimulation pulse output means 86 is connected to a terminal c. The terminal c is connected to a region of a living body via conductors or electrodes.

Figure 9A:
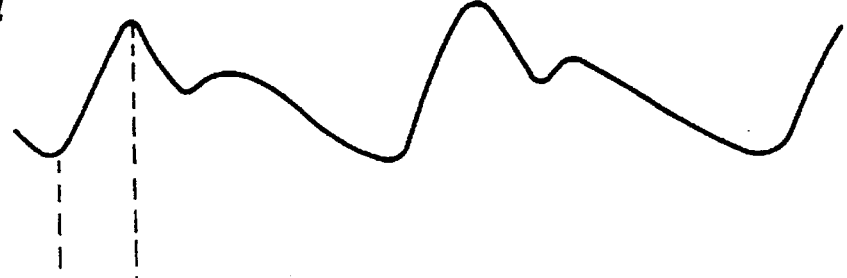
FIGS. 9a to 9c show waves detected in the components shown in the block diagram of FIG. 8.
Figure 9B:
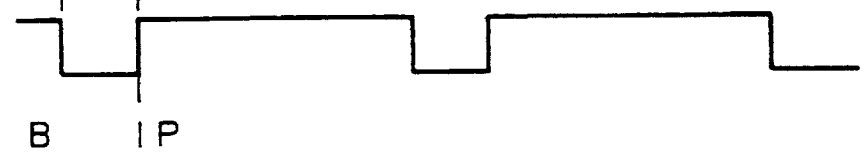
Figure 9C:
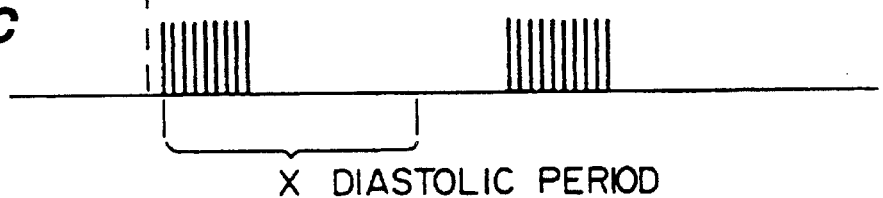

The pulse wave input means 81 inputs a pulse wave signal via the aforesaid sensor through an earlobe or a fingertip, and outputs a pulse wave electric signal shown in FIG. 9a. The pulse wave electric signal is passed to the pulse wave pulse producing means 82. The pulse wave pulse producing means 82 then produces pulses each of which is defined with the peak potential P and bottom potential B, and outputs pulses like those shown in FIG. 9b. The pulse wave pulses are fed to the diastolic period producing means 84. The diastolic period producing means 84 then detects a diastolic period X shown in FIG. 9c for each pulse wave pulse. The data of diastolic periods X are fed to the electric stimulation pulse output means. The electric stimulation pulse output means 86 outputs a series of pulses having an amplitude of up to about 200 volts and a frequency of up to several tens of hertz via the output terminal c during part of or the whole of each diastolic period. FIG. 9c shows an example of the output.

Figure 9D:
Figure 9E:
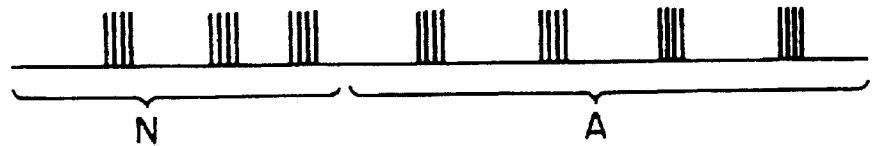

The pulse wave duration measuring means 83 measures a pulse duration of an output pulse of the pulse wave pulse producing means 82, and outputs the value to the control means 85. The control means 85 monitors all the pulse duration values. When a pulse duration becomes narrower (A) than the pulse duration of a normal pulse (N) as shown in FIG. 9d and takes on a smaller value than a specified value, the control means 85 provides the electrical stimulation pulse output means 86 with a signal to output electrical stimulation pulses during every other pulse duration. In response to the signal, the electrical stimulation pulse output means 86 outputs, as shown in FIG. 9e, a stimulation pulse during every other pulse duration. A stimulation pulse is output during every other pulse duration. Alternatively, a stimulation pulse may be output after every two, three, or more pulse durations.

Figure 5:
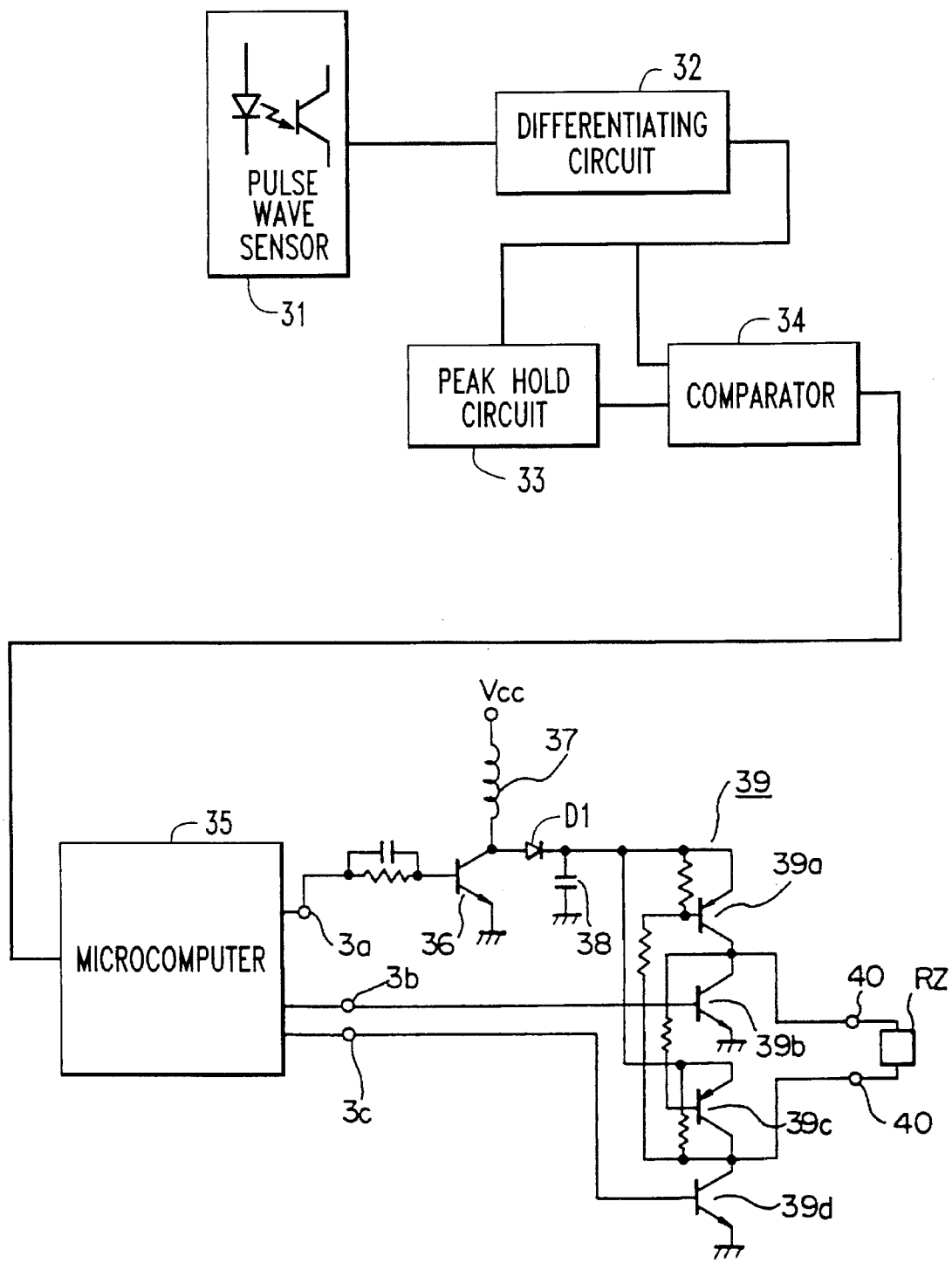
FIG. 5 is a block diagram of another example relating to the first aspect of the present invention.

The particular circuitry of this example is identical to that shown in FIG. 5. In FIG. 5, 31 denotes a pulse wave sensor made up of a light emitting diode (cds or LED) and a phototransistor. The pulse wave sensor 31 converts a change in light resulting from a blood flow into an electric change, and outputs the electric change.

In the aforesaid example, the pulse wave duration measuring means 83, diastolic period producing means 84, control means 85, and electrical stimulation pulse output means 86 are partly run according to programs installed in the microcomputer 35. The programs may have any processing flows as long as the operations of the embodiment shown in FIG. 8 are executed.

As described above in detail, this example generates pulse wave pulses using a pulse wave sensor. When the pulse duration of a pulse wave pulse becomes smaller than a specified value, electrical stimulation pulses are output during every other or two or more pulse durations. Consequently, a load to the heart is minimized, and electrical stimulation can be applied to a living body for a prolonged period of time.

The present invention detects a specific biomedical signal in order to generated electrical stimulation pulses. In the aforesaid-examples, a pulse wave is used as the biomedical signal. The present invention is not limited to the pulse wave but enables the use of any biomedical signal such as an electrocardiogram or pulses.

In the present invention, a biomedical signal detecting means for detecting the pulse wave as a biomedical signal is not limited to the aforesaid arrangement. Any detecting means can be employed as long as it is constituted to achieve the objects of the present invention.

Figure 10:
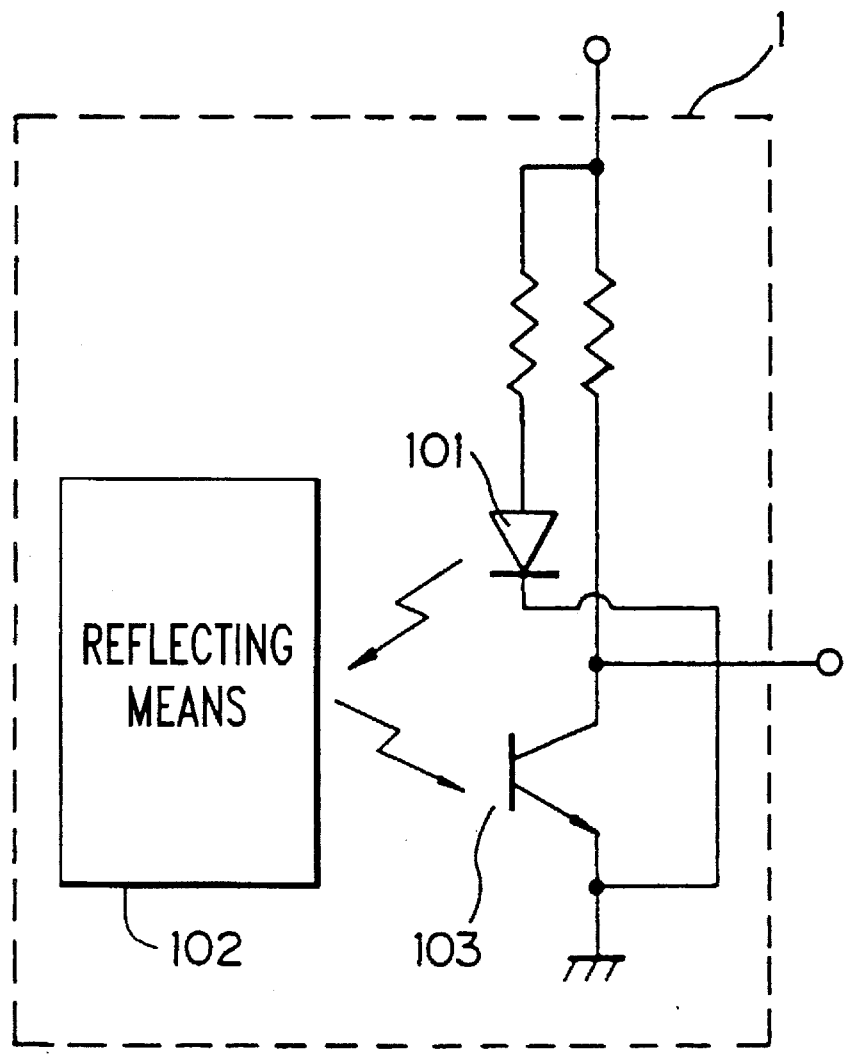
FIG. 10 is a circuit diagram showing an example of a configuration of a biomedical signal detecting means used in the present invention.

For example, when a photoelectric transfer transistor is employed as the biomedical signal detecting means in the present invention, as shown in FIG. 10, the biomedical signal detecting means consists of a light emitting diode 101 realized with a light emitting element, a reflecting means 102, and a light receiving transistor 103. The light emitting diode 101 and reflecting means 102 may be structured so as to allow blood to flow between them.

Figure 11:
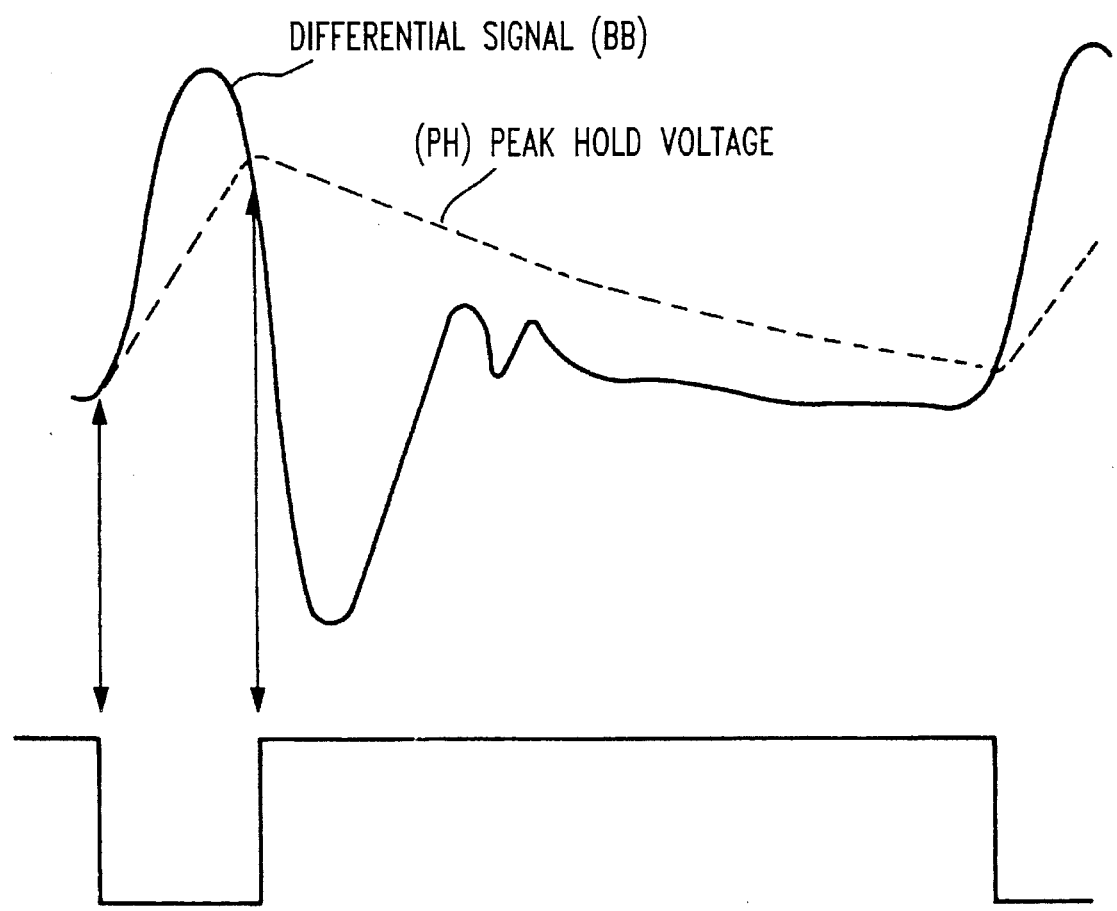
FIG. 11 is a graph showing a shift of a peak hold voltage relating to the second aspect of the present invention.

In the present invention, as shown in the aforesaid examples, a differential signal of a pulse wave is compared with a peak hold value of the differential signal, so that the end of a systolic period SS in the pulse wave and the end of a diastolic period KK therein can be identified or detected reliably. In FIG. 11, the peak hold value of a differential signal is set to decrease relative to the differential signal BB for a specified time constant. The differential signal BB is compared with the peak hold value PH using a comparator. When the differential value BB exceeds the peak hold value PH, a systolic SS pulse is forced to fall. When the differential value BB becomes smaller than the peak hold value PH, a systolic SS pulse is forced to rise. This results in a systolic SS pulse shown in FIG. 11.

Figure 12:
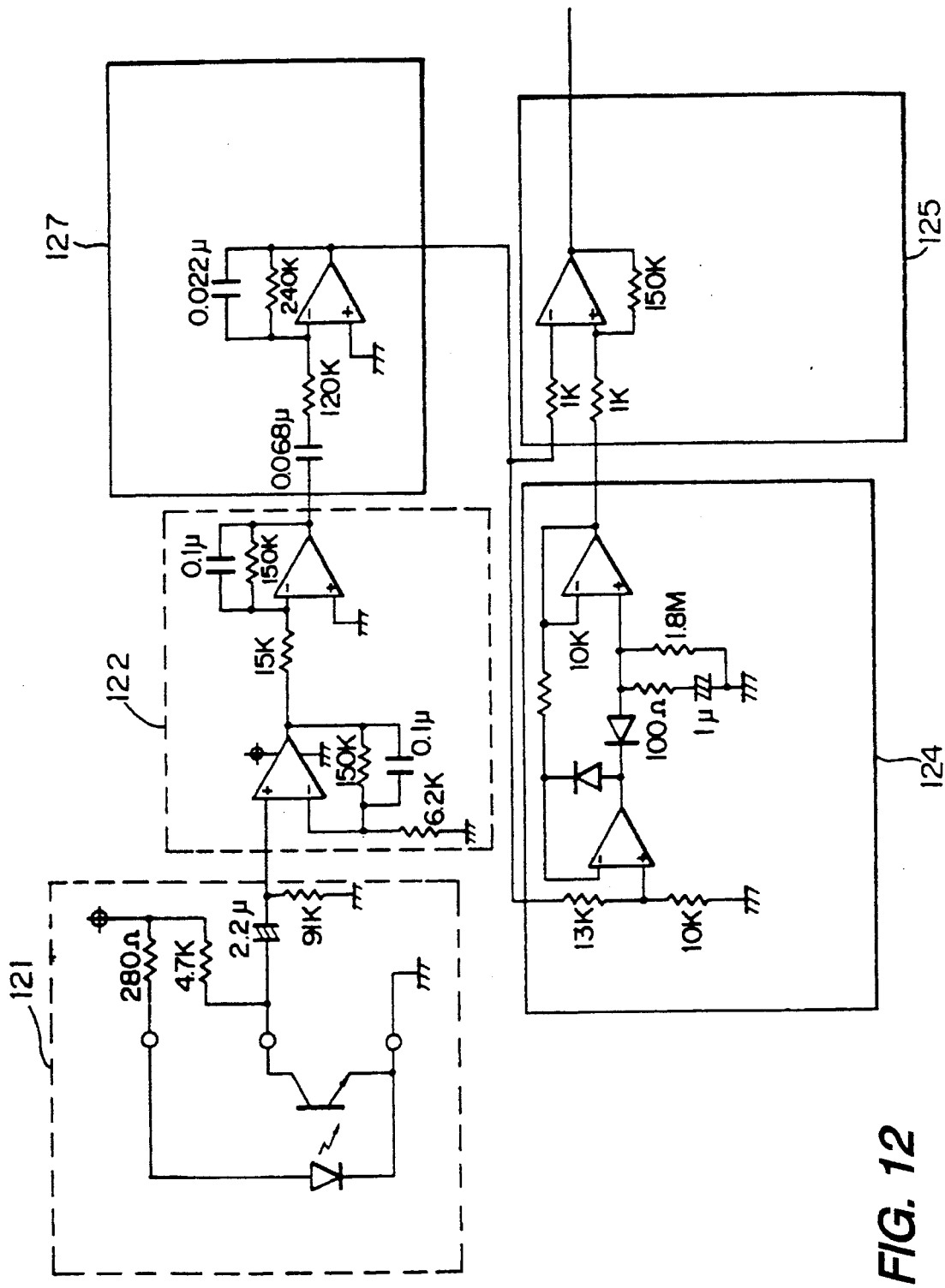
FIG. 12 is a block diagram showing an example of a configuration of a differentiating means, a peak hold means, and a comparing means relating to the second aspect of the present invention.

FIG. 12 shows an example of a particular circuitry for executing comparison in the present invention.

In FIG. 12, an output of a pulse wave sensor 121 is amplified by a filter amplifying means 122, and input to a known differentiating means 127.

Also included are a peak hold means that holds all peak voltage values or differential values of outputs of the differentiating means 127 and that decreases each of the peak hold values for a specified time constant, and a comparing means 125 that inputs the outputs of the differentiating means 127 and peak hold means 124, and outputs specified logical data.

The fourth aspect of an electrical stimulator relating to the present invention will be described in conjunction with an example.

The aforesaid stimulator is usually put on the abdomen and used continuously or intermittently for a prolonged period of time ranging from thirty minutes to eight hours, thus providing the aforesaid advantages. The prolonged use is accompanied by a drawback a conventional electrical stimulator does not have. During conduction, charges are stored in the vicinity of a conducting region of a human body. The charges are released during periods corresponding to pulse durations of electrical stimulation pulses provided. In, for example, a low-frequency treatment apparatus providing electrical stimulation pulses having long pulse durations, such a problem as storage of charges therefore does not occur. However, in reality, the charges are not relieved perfectly. Some charges remain, which does not pose a problem for a short use. For a prolonged use, however, the charges cause the skin to redden or get burnt. In an effort to eliminate the charges, a depolarization means has been proposed. The depolarization means has a circuitry in which an electrical switching element is used to short-circuit between different or indifferent conductors during pulse durations of electrical stimulation pulses. The electrical switching element has on-state resistance, whereby after electrical stimulation with high energy is applied, charges are not released completely. The depolarization means is therefore not very useful for a prolonged use. Another depolarization means for applying pulses of a reversed polarity, which is not an electrical stimulator, has been proposed. The mere application of reversed pulses is not very effective, in particular, when stimulation pulses having high energy; such as, electrical stimulation pulses are applied to a human body for a prolonged period.

According to the third aspect of the present invention, polarization can be resolved by substantially equalizing the magnitude of each of positive stimulation pulses among electrical stimulation pulses, which are produced during pulse durations of pulse wave pulses, with the magnitude of each of negative stimulation pulses. What is referred to as a "magnitude" in the present invention is a value determined by a pulse amplitude and a pulse width of an electrical stimulation pulse. In addition, the magnitudes are "substantially equalized," because the output state of a stimulation pulse varies depending on the state of a pulse wave. If the magnitudes are set to be substantially equal to each other so as to cancel out the variation, polarization can be resolved successfully.

The circuitry of an example according to the fourth aspect of the present invention is identical to the one shown in FIG. 5. The operations of an example according to the fourth aspect will be described in conjunction with the circuitry in FIG. 5 with reference to FIGS. 13a to 13e.

Figure 13A:
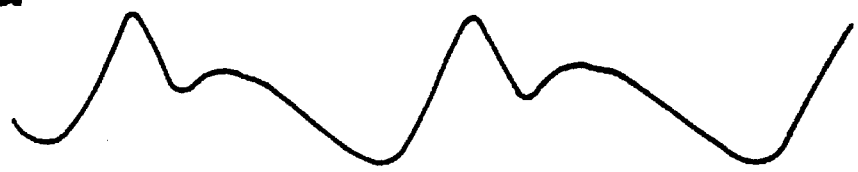
FIGS. 13a to 13e show waves detected in the components relating to the fourth aspect of the present invention.
Figure 13B:

The pulse wave sensor 31, which is put on any region of a living body, converts a blood flow change into a potential change (wave of FIG. 13a). The potential change is converted into a current signal and fed to the differentiating circuit 32. A blood flow signal is converted into a differential signal by the differentiating circuit 32, and supplied to one terminals of the peak hold circuit 33 and comparator 34.

With the input of a peak of the differential signal, the peak hold circuit 33 outputs a voltage in which the peak potential is held. The voltage is fed to the other terminal of the comparator 34.

The comparator 34 compares the potential of the differential signal provided by the differentiating circuit 32 with that of the output signal of the peak hold circuit 33. When a specified potential difference occurs, the comparator outputs a pulse (wave of FIG. 13b). The pulse has a pulse width defined with a leading edge corresponding to the peak potential and a trailing edge corresponding to the bottom potential.

The microcomputer 35 accepts the pulse, delays the rise of the pulse by several microseconds to several tens of milliseconds, and produces a pulse whose rise is delayed. The pulse width of the delayed pulse is regarded as an electrical stimulation output permissible period. The microcomputer 35 outputs drive pulses via the terminals 3a, 3b, and 3c. The pulse supplied via the terminal 3a is a rectangular pulse having a frequency of several kilohertz. With the pulse, the transistor 36 is turned on or off. When the transistor 36 is turned on or off, the current flowing through the inductor 37 is cut off. When the current is cut off, the inductor 37 generates a back electromotive force which is then stored in the capacitor 38 via the diode.

Figure 13C:
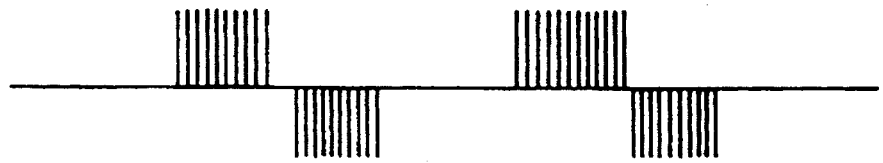
Figure 13D:
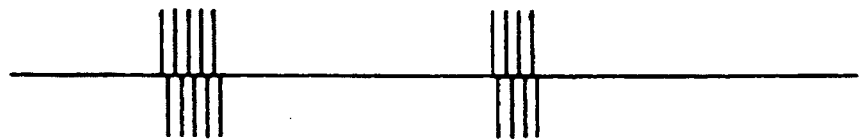
Figure 13E:
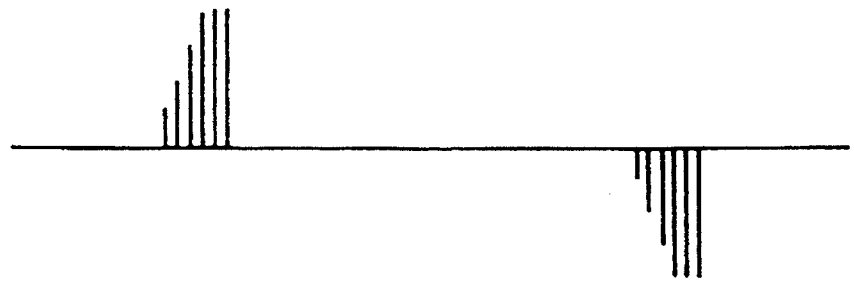

The rectangular pulses having frequencies of several hertz are supplied via terminals 3b and 3c. When a pulse is supplied via the terminal 3b, the transistors 39b and 39c are turned on and off repeatedly. The charges stored in the capacitor 38 are released via the transistor 39c, output terminal 40, load RZ, and transistor 39b. As a result, a positive electrical stimulation pulse is produced. When a pulse is supplied via the terminal 3c, the transistors 39a and 39d are turned on and off repeatedly. The charges stored in the capacitor 38 are released via the transistor 39a, output terminal 40, load RZ, and transistor 39d. As a result, a negative electrical stimulation pulse is produced (wave of FIG. 13c). At this time, the magnitude of an electrical stimulation pulse supplied via the terminal 3b should merely be substantially equal to that of an electrical stimulation pulse supplied via the terminal 3c. Various modes have been proposed. For example, the wave of FIG. 13c is formed by continuously outputting a positive stimulation pulse during every pulse wave pulse duration via the output terminal, and then outputting the same number of electrical stimulation pulses by reversing the polarity from negative to positive. The wave of FIG. 13d is formed by outputting positive and negative electrical stimulation pulses alternately. The wave of FIG. 13e is formed by applying positive and negative electrical stimulation alternately for every other pulse wave. Depending on whether the microcomputer 35 outputs a drive pulse via the terminal 3b or 3c, the polarities of electrical stimulation pulses supplied via the output terminal 40 vary. The drive pulses are produced according to a program installed in the microcomputer 35. The contents of the program are not limited to specific ones, as long as it is programmed that each of the drive pulses supplied via the terminals 3b and 3c maintains the number of pulses, pulse duration, and pulse width substantially unchanged during an output time. What is referred to as an "output time" indicates a total output time or a time marked by unit times.

As described above, this example produces pulse wave pulses using a pulse wave sensor, outputs electrical stimulation pulses during the pulse durations of the pulse wave pulses. At this time, the magnitude of each positive stimulation pulse is substantially equalized with the one of each negative stimulation pulse, which resolves polarization. Eventually, electrical stimulation pulses can be applied to a human body continuously or intermittently for a prolonged period of time.

The fifth aspect of the present invention will be described below.

In the aforesaid example, a biomedical signal such as an electrocardiogram or pulses is used to detect diastolic periods. Stimulation is then applied mainly during the diastolic periods, whereby blood circulation can be accelerated effectively compared with that in a conventional electrical massager, low-frequency treatment apparatus, and other various electrical stimulators. Besides, acceleration of blood circulation leads to weight reduction.

A sensor for detecting a pulse wave is mechanically fitted to an earlobe or a fingertip, which, therefore, comes off easily. When the pulse wave sensor comes off, stimulation is applied to a living body unexpectedly. This incident must be avoided. The aforesaid stimulator should preferably be used for a prolonged period of time. The stimulator is therefore used while a person is asleep. The unexpected application of stimulation resulting from a missing sensor must be avoided.

According to the fifth aspect of the present invention, even when a pulse wave sensor comes off, stimulation will not be applied unexpectedly. The underlying idea is that when a pulse wave sensor comes off, an average pulse duration of an electric signal generated by the pulse wave sensor becomes abnormally longer or shorter than a general pulse duration of a pulse wave. Specifically, multiple pulse durations of a pulse wave are added up and averaged. An upper limit of an average value and a lower limit of an average value are then defined. When a pulse duration is within the limits, application of electrical stimulation to a living body is enabled. When a pulse duration exceeds the limits, generation of electrical stimulation pulses is stopped.

An example according to the fifth aspect of the present invention will be described below.

Figure 14:
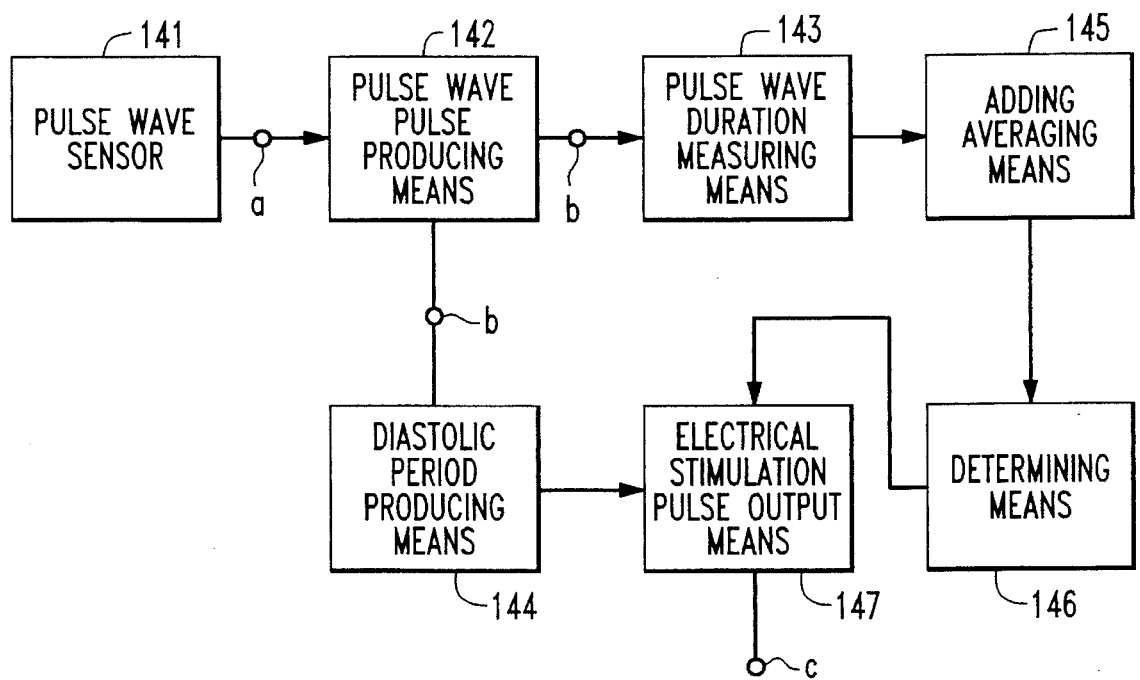
FIG. 14 is a block diagram of an example relating to the fifth aspect of the present invention.

FIG. 14 is a block diagram showing a configuration of an example according to the fifth aspect.

141 denotes a pulse wave sensor that is a sensor realized with a photoelectric transducer, piezoelectric transducer, or the like. The pulse wave sensor is put on an earlobe, finger, arm, or the like, and converts a pulse wave into an electric signal.

142 denotes a pulse wave pulse producing means for producing pulse wave pulses using the pulse wave electric signal. The pulse wave pulse producing means 142 detects every peak potential and bottom potential in a pulse wave, and produces pulses each of which rises with a peak potential and falls with a bottom potential, and vice versa.

143 denotes a pulse wave duration measuring means that measures and outputs a pulse duration of an output pulse of the pulse wave pulse producing means.

144 denotes a diastolic period producing means that calculates or detects a diastolic period using the output of the pulse wave pulse producing means.

145 denotes an adding averaging means that adds up multiple pulse durations provided by the pulse wave duration measuring means, divides the sum by the number of pulse durations, and then outputs a signal representing the average value. "Multiple pulse durations" means a predetermined number of pulse durations or any number of pulse durations determined according to the situation, for example, 2, 4, 8, or 16.

146 denotes a determining means that determines whether a value output by the adding averaging means is within a specified range. If the value exceeds the specified range, a signal indicating to stop the output of electrical stimulation pulses is supplied. The "specified range" is a range of fluctuation in normal person's pulse rate.

147 denotes an electrical stimulation pulse output means that outputs electrical stimulation pulses according to an output signal of the diastolic period producing means 144. In response to the input of a stop signal sent from the determining means 146, the electrical stimulation pulse output means 147 stops the output of electrical stimulation pulses. The electrical stimulation pulse output means 147 keeps stopping the output until the determining means 146 releases the stop signal.

The pulse wave sensor 141 is connected to the pulse wave pulse producing means 142 via a terminal a. The pulse wave pulse producing means 142 is connected to each of the pulse wave duration measuring means 143 and diastolic period producing means 144 via a terminal b. The pulse wave duration measuring means 143 is connected to the adding averaging means 145. The adding averaging means 145 is connected to the determining means 146. The diastolic period producing means 144 and determining means 146 are connected to the electrical stimulation pulse output means 147. The electrical stimulation pulse output means 147 is connected to a terminal c. The terminal c is connected to a region of a living body via conductors, electrodes, or the like.

Figure 15A:
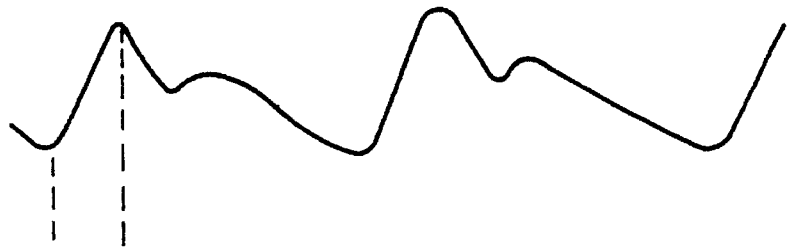
FIGS. 15a to 15f show waves detected in the components shown in the block diagram of FIG. 14.
Figure 15B:
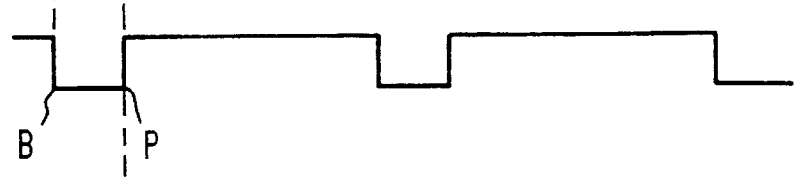
Figure 15C:
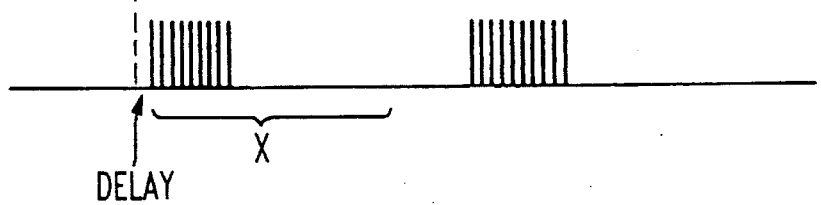
Figure 15D:
Figure 15E:
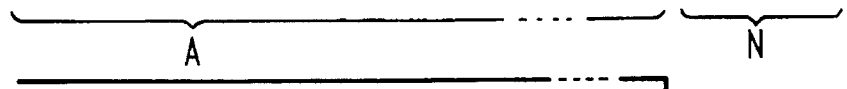
Figure 15F:
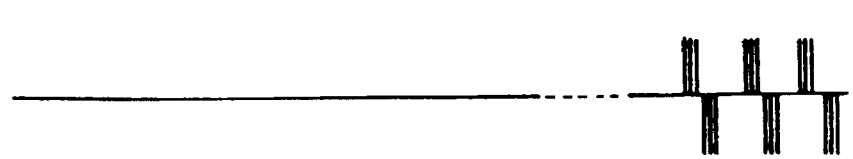
Figure 16:
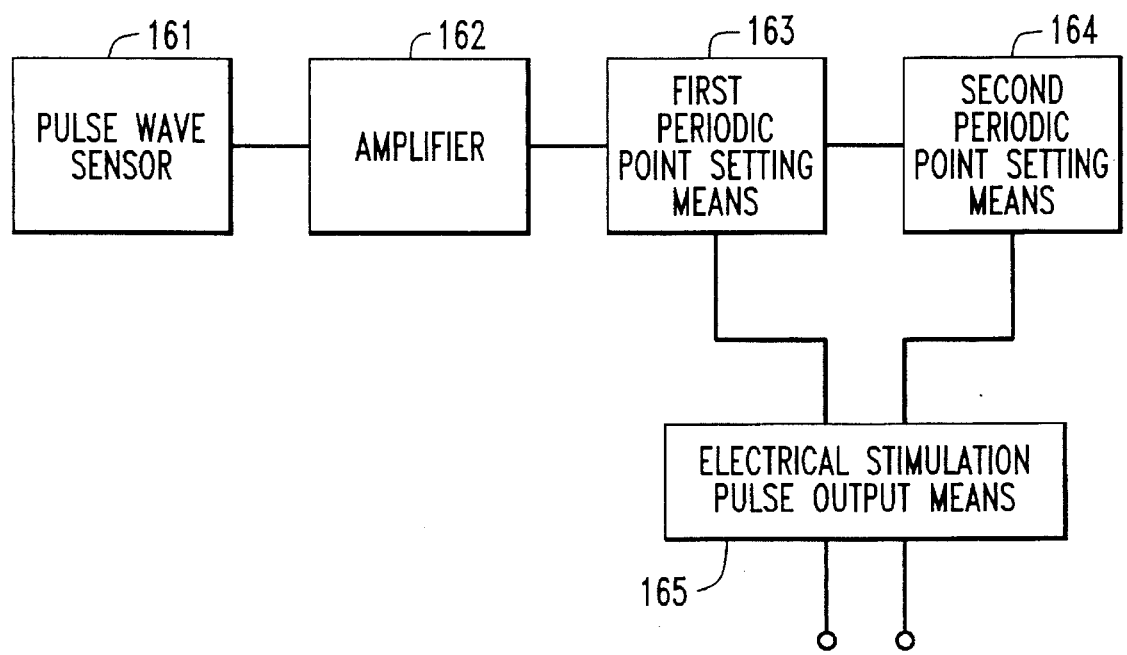
FIG. 16 is a block diagram of an example relating to the sixth aspect of the present invention.

The pulse wave input means 141 inputs a pulse wave signal from an earlobe, finger, or the like via a sensor, and outputs a pulse wave electric signal like the wave shown in FIG. 15a. The pulse wave electric signal is fetched into the pulse wave pulse producing means 142 which then produces a pulse rising with the peak potential P of the pulse wave electric signal and falling with the bottom potential B thereof. The pulses constitute a wave like the wave in FIG. 15b. A pulse wave pulse is fed to the diastolic period producing means 144 which then detects a diastolic period X as shown in the wave in FIG. 15c. The diastolic period X is fed to the electrical stimulation pulse output means which then outputs a pulse having an amplitude of up to about 200 volts and a frequency of up to several tens of hertz via the output terminal c during part or the whole of the diastolic period. An example of the output is shown as the wave in FIG. 15c.

The pulse wave duration measuring means 143 measures a pulse duration of an output pulse of the pulse wave pulse producing means 142, and outputs the pulse duration value to the adding averaging means 145. The adding averaging means 145 adds up and averages multiple outputs, and outputs a signal representing an average value to the determining means 146. The determining means 146 monitors every average value to see if the average value is within a specified range. When the pulse wave sensor comes off, the pulse wave pulse producing means 142 provides pulses as shown as A of a wave 15d in FIG. 15. In the meantime, the determining means 146 keeps outputting stop pulses shown as a wave 15e in FIG. 15 to the electrical stimulation pulse output means 147. While inputting this signal, the electrical stimulation pulse output means 147 stops outputting. When the pulse wave sensor is placed in a normal state N and a signal supplied by the adding averaging means 145 enters the specified range set in the determining means 146, the electrical stimulation pulse output means 147 restarts outputting.

The circuitry of this example is fundamentally identical to the one shown in FIG. 5. An operation program installed is, however, different from the one in the previous example.

The operations of this example according to the fifth aspect of the present invention will be described with reference to FIG. 5.

The pulse wave sensor 31 is put on any region of a living body and converts a blood flow change into a potential change. The potential change is converted into a current signal, and then fed to the differentiating circuit 32. The blood flow signal is converted into a differential signal by the differentiating circuit 32, and then supplied to terminals of the peak hold circuit 33 and comparator 34.

With the input of a peak of the differential signal, the peak hold circuit 33 outputs a voltage in which the peak potential is held. The voltage is fed to the other terminal of the comparator 34.

The comparator 34 compares the potential of the differential signal provided by the differentiating circuit 32 with that of the output signal of the peak hold circuit 33. When a predetermined potential difference occurs, a pulse is output. The pulse has a pulse width defined with a leading edge corresponding to the peak potential of the differential signal and a trailing edge corresponding to the bottom potential thereof.

The microcomputer 35 inputs the pulse, and delays the rise of the pulse by several microseconds to several tens of milliseconds. A period from the delayed point to the fall of the pulse wave pulse fed to the microprocessor 35 is regarded as an electrical stimulation output permissible period. The microprocessor 35 outputs drive pulses via the terminals 3a, 3b, and 3c during the permissible period. The pulse supplied via the terminal 3a is a rectangular pulse having a frequency of several kilohertz. With the pulse, the transistor 36 is turned on or off. When the transistor 36 is turned on or off, the current flowing through the inductor 37 is cut off. When the current is cut off, the inductor 37 generates a back electromotive force which is then stored in the capacitor 38 via the diode.

Rectangular pulses with several hertz are output via the terminals 3b and 3c. When a pulse is output via the terminal 3b, the transistors 39b and 39c are turned on and off repeatedly. The charges stored in the capacitor 38 are released via the transistor 39c, output terminal 40, load RZ, and transistor 39b. When a pulse is output via the terminal 3c, the transistors 39a and 39d are turned on and off repeatedly. The charges stored in the capacitor 38 are released via the transistor 39a, output terminal 40, load RZ, and transistor 39d. Depending on whether a pulse is output via the terminal 3b or via the terminal 3c, the electrical stimulation pulse supplied via the output terminal 40 has a reversed polarity.

According to the pulse output by the microcomputer 35 via the terminal 3a, 3b, or 3c, electrical stimulation pulses are supplied via the output terminal 40. The polarity of the electrical stimulation pulse varies depending on whether the pulse is output via the terminal 3b or 3c. When the pulses provided via the terminal 3a, 3b, or 3c have different pulse widths or durations, varying electrical stimulation can be supplied via the output terminal 40. The pulse wave duration measuring means 143, diastolic period producing means 144, adding averaging means 145, determining means 146, and electrical stimulation pulse output means 147, which are shown in FIG. 14, are partly run according to programs installed in the microcomputer 35. The programs may have any processing flows as long as the operations of this example shown in FIG. 14 are executed.

As described above, this example produces a pulse wave pulse using a pulse wave sensor, and adds up and averages pulse durations of the pulse wave pulses. When the average value exceeds a specified range, an abnormal state resulting from a missing pulse wave sensor is identified. The output of electrical stimulation pulses is stopped until a normal state is re-set, which enables stable output of electrical stimulation pulses without unexpected application of stimulation to a human body.

Next, the sixth aspect of an electrical stimulator according to the present invention will be described. In the aforesaid examples, a pulse wave is monitored as a biomedical signal, and electrical stimulation pulses are applied to a living body during the systolic periods SS of the pulse wave and then during the diastolic periods KK thereof.

In order to detect a diastolic period, as apparent from the wave shown in FIG. 1, a systolic period SS is detected, and then a period except the systolic period is detected as a diastolic period KK. In order to detect the systolic period SS, a second peak must be detected in a pulse wave. However, the second peak is very small. When detected by a pulse wave sensor, the second peak is decayed due to an artifact or a constant of an electric circuit, which depends on the sensitivity of the pulse wave sensor though. Steady detection of the second peak is therefore hard to do.

In a portable stimulator, the number of component parts must be minimized. It is therefore substantially impossible to improve the accuracy in resolving a pulse wave. Incorporation of sophisticated devices leads to an increase in the time required for detecting a diastolic period, which eventually reduces the time for which stimulation is applied.

According to the sixth aspect of the present invention, based on the idea that a systolic period is a substantially constant time interval, a signal is produced to start at a point interposed between the rise and peak (first periodic point) of a pulse wave signal or a differentiating signal resulting from the differentiation of the pulse wave signal, and end forcibly at a point (second periodic point) separated by a specified time interval from the first periodic point. Thus, a pulse wave signal representing a systolic period is produced. Biomedical stimulation pulses are output during the whole or part of each period between the end and start of the signal; that is, each diastolic period KK. Thus, a biomedical stimulation pulse generator capable of generating pulses precisely during diastolic periods is materialized. The foregoing "signal to be produced" represents a numerical value or a program routine when a microcomputer is concerned, or pulses when circuits are concerned. The start point of a systolic period on the pulse wave is, as shown in FIG. 1, a minimum or maximum potential of the pulse wave, or an intermediate potential between the minimum and maximum potentials. In reality, the rise of a pulse wave detected by a pulse wave sensor is very steep but not so smooth as shown in FIG. 1. The start point (first periodic point) may be any point within a certain range.

The first periodic point and second periodic point may refer to the leading and trailing edges of a pulse, or represent different pulses.

A "biomedical stimulation pulse" is a pulse or electric energy that is converted into a physical vibration for applying electrical stimulation directly to a living body. In the embodiments described later, an output forming means for applying electrical stimulation to a living body will be described. A stimulation pulse generating means installed in the succeeding stage is a mere embodiment, which may be replaced with a vibrator for an electrical massager.

An example according to the sixth aspect of the present invention will be described with reference to FIGS. 16 and 17a to 17d.

161 denotes a pulse wave sensor that is realized with a photoelectric transducer or a piezoelectric transducer. The pulse wave sensor 161 is put on an earlobe, finger, arm, or the like, and converts a pulse wave into an electric signal.

162 denotes an amplifier that amplifies an electric signal representing a pulse wave acquired by the pulse wave sensor.

163 denotes a first periodic point setting means that detects a first periodic point in the pulse wave signal and outputs pulses or any other signal. The first periodic point setting means 163 detects a first periodic point; that is, the peak or bottom of the pulse wave or a differentiating wave resulting from the differentiation of the pulse wave, or any point near the peak or bottom, and then outputs pulses or any other signal. 164 denotes a second periodic point setting means that sets a second periodic point which is separated by any time interval from the first periodic point specified in an input pulse wave signal, and outputs the set second periodic point. When a signal provided by the second periodic point setting means 164 is a pulse signal, the rise or fall of a pulse, or a pulse itself represents a second periodic point. This is also true for the first periodic point.

165 denotes an electrical stimulation pulse output means that outputs electrical stimulation pulses during the whole or part of each period from the second periodic point set by the second periodic point setting means 164 to the first periodic point set by the first periodic point setting means 163.

The electrical stimulation pulse output means 165 should merely output stimulation pulses at least during diastolic periods (periods each lasting from the second periodic point to the first periodic point). Stimulation pulses are output in any appropriate output mode.

In addition to the above description, from a viewpoint of practicability, the following must be noted: the output of electrical stimulation pulses during periods each lasting from the second periodic point to the first periodic point equals to the output of electrical stimulation pulses during diastolic periods, and also means that electrical stimulation pulses should never be applied during systolic periods. That is to say, since violent exercise results in an increased pulse rate and shortened diastolic periods, the operations of detecting diastolic periods and applying electric stimulation during the diastolic periods become meaningless. An electrical stimulator according to the present invention is often used for a prolonged period of time. Even when the electrical stimulator is used for a short period of time, the advantages available when some stimulation pulses are applied during systolic periods does not differ drastically from the ones available when no stimulation pulses are applied.

What is important is that stimulation applied during a total of diastolic periods must be apparently higher in density than that during a total of systolic periods.

Next, the operations will be described.

Figure 17A:
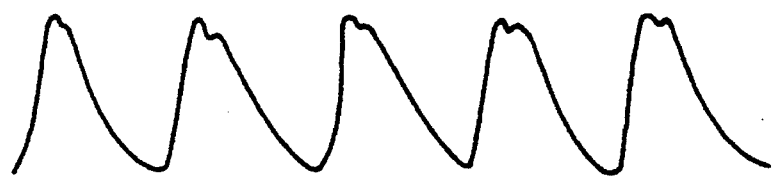
FIGS. 17a to 17d show waves detected in the components shown in the block diagram of FIG. 16.

The wave in FIG. 17a of an electric pulse wave signal provided by the pulse wave sensor 161 is amplified by an amplifier, and then fed to the first periodic point setting means 163.

Figure 17B:
Figure 17C:
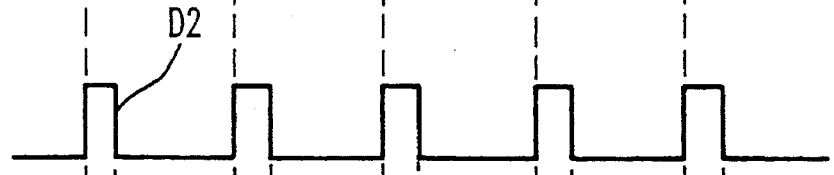
Figure 17D:
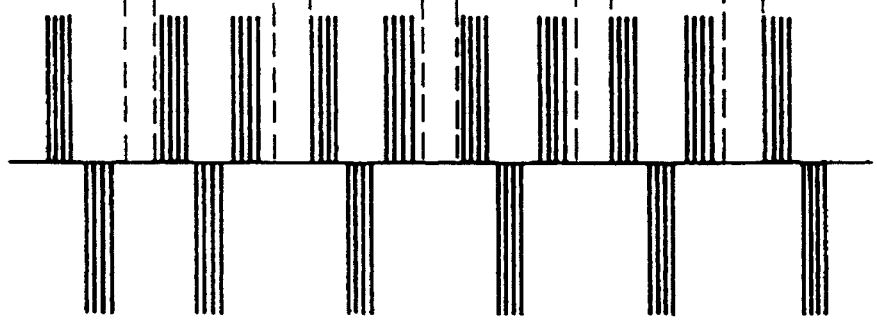

The first periodic point setting means 163 detects a peak value or bottom value, or any value around the peak or bottom in the input pulse wave signal, raises an output, sets a first periodic point D1, and then outputs the set first periodic point D1 (wave in FIG. 17b). The second periodic point setting means 164 then sets and outputs a second periodic point D2 after a specified time interval of several microseconds to several tens of milliseconds from the first periodic point provided by the first periodic point setting means 163. A pulse wave signal shown as the wave in FIG. 17c ensues. The electrical stimulation pulse output means 165 outputs stimulation pulses each having a pulse width of several hundreds of microseconds and a pulse amplitude of up to 200 volts, which form the wave like a wave shown in FIG. 17d, during periods each lasting from D2 to D1.

The pulse width of a stimulation pulse is several hundreds of microseconds, while the pulse width during each diastolic period is several hundreds of milliseconds which is about a thousand times larger. Stimulation pulses can therefore be realized in various modes.

The circuitry in this example is substantially identical to the one shown in FIG. 5. The operations of this example are substantially identical to those described in conjunction with FIG. 5. The detailed description will therefore be omitted.

As mentioned above, the example according to the sixth aspect of the present invention permits precise detection of systolic periods, and shortens the processing time for detection. Electrical stimulation pulses can therefore be locked onto diastolic periods.

Next, the seventh aspect relating to an electrical stimulator according to the present invention will be described.

In any of the aforesaid examples, a biomedical signal such as a pulse, a pulse wave, or an electrocardiogram is used to detect, for example, diastolic periods of the heart. Stimulation is applied mainly during diastolic periods, which permits effective acceleration of blood circulation not comparable with that in a conventional electrical massager, electrical stimulator, or low-frequency treatment apparatus. Moreover, weight reduction may be expected.

However, when a signal originating from a living body is detected, a problem arises concerning how to handle noises (artifacts) occurring in a pulse wave detector, electrodes or any other sensor, and other components thereabout.

Employment of a filter has been discussed. For artifacts having frequency components and amplitudes similar to those of a biomedical signal, there is a limit in the capability for removing the artifacts.

According to the seventh aspect of the present invention, multiple pulse durations are detected in a biomedical signal such as a pulse wave detected by a sensor, and then averaged. A pulse duration of an ongoing signal is subtracted from the average value, and a resultant difference is compared with a threshold derived from the average value. Using the threshold as a reference, the occurrence of an artifact is detected reliably.

Figure 18:
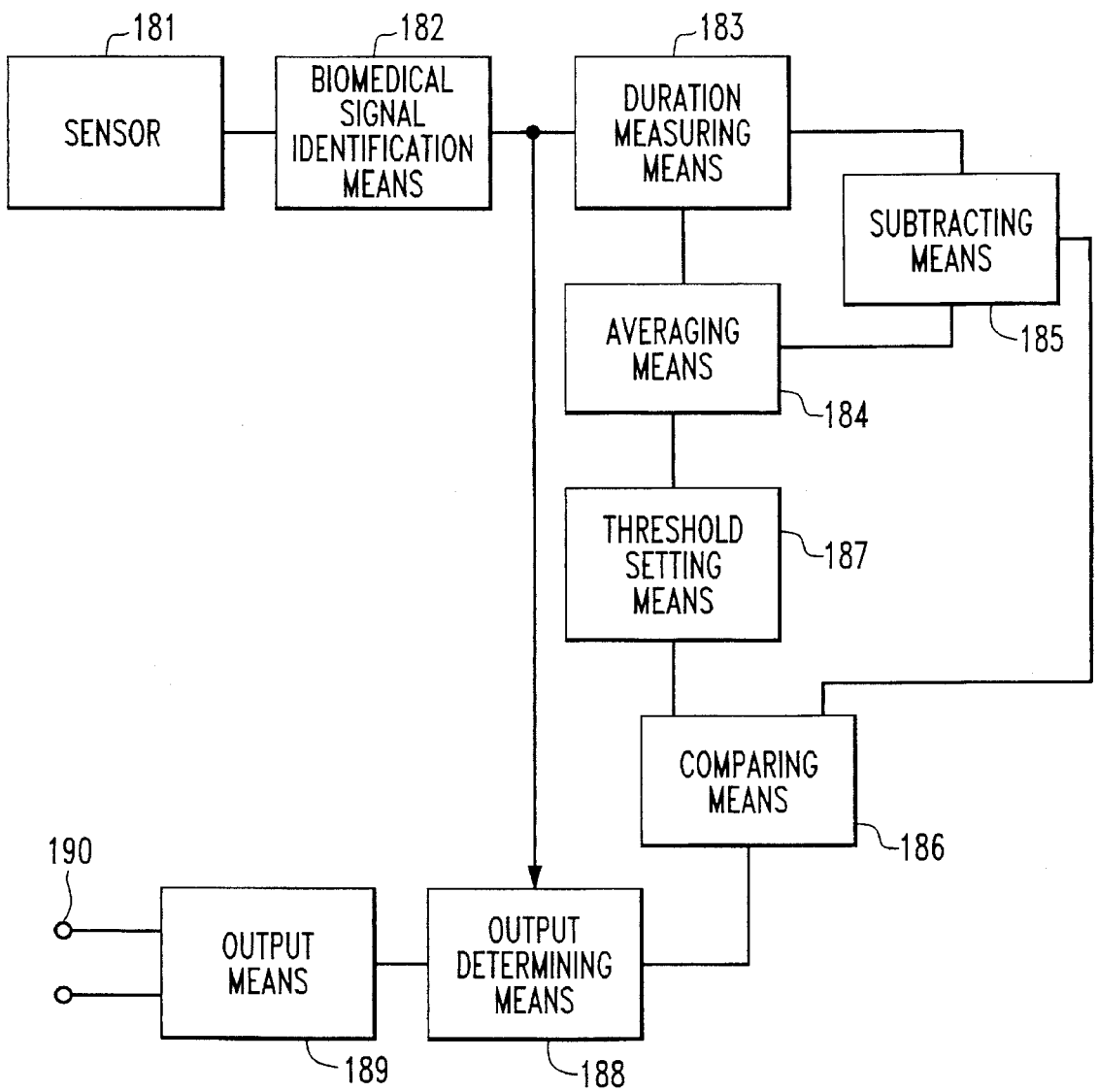
FIG. 18 is a block diagram of an example relating to the seventh aspect of the present invention.

FIG. 18 is a block diagram showing a configuration of an example according to the seventh aspect of the present invention.

181 denotes a sensor that varies depending on a biomedical signal to be measured. The sensor 181 is, for example, a photoelectric transducer or electrodes. The sensor 181 is put on an earlobe, fingertip, chest, hand, or foot.

182 denotes a biomedical signal identification means that is a means for identifying an R wave of an electrocardiogram or every peak of a pulse wave, and outputting an identification pulse.

183 denotes a duration measuring means that is a means for measuring a cycle, duration, or frequency of a pulse or an electrocardiogram and outputting a duration signal representing the measured value.

184 denotes an averaging means that fetches multiple input duration signals, averages them, and then outputs an average signal.

185 denotes a subtracting means that performs a subtraction between the duration signal provided by the duration measuring means 183 and the average signal provided by the averaging means 184, and outputs a difference signal.

186 denotes a comparing means that inputs a threshold signal provided by a threshold setting means 187 and the difference signal provided by the subtracting means, compares between the signals, and outputs a result-of-comparison signal.

187 denotes a threshold setting means that sets an appropriate ratio or fixed value for a value provided by the averaging means 184, and outputs a threshold signal.

188 denotes an output determining means that inputs the result-of-comparison signal from the comparing means 186 and the identification pulse from the biomedical signal identifying means 182. Unless the result-of-comparison signal represents an artifact, the output determining means 188 outputs the identification pulse.

189 denotes an output means that outputs an electric signal, which has a capability for stimulating a human body, according to the output pulse of the output determining means 188. The output means 189 may be a boosting pulse generator made up of a boosting element such as a coil or a transformer and a driver for causing the boosting element to boost voltage, a boosting pulse generator made up of a boosting element such as a coil or a transformer, a storage element for storing boosting energy; such as, a capacitor, and a driver for driving these elements, or a transducer for converting stimulation pulses into mechanical vibrations.

Next, the operations of this example will be described.

A biomedical signal detected by the sensor 181 is converted into pulses by the biomedical signal identifying means 182, and then supplied to each of the duration measuring means 183 and output determining means 188. With the pulse, the duration measuring means 183 provides a signal representing a pulse duration. The duration signal provided by the duration measuring means 183 is input to each of the averaging means 184 and subtracting means 185. The averaging means 184 adds the input duration signal to the duration signals which have been input so far, averages the signals, and then outputs an average signal to each of the subtracting means 185 and threshold signal setting means 187. The subtracting means 185 subtracts the average signal provided by the averaging means 184 from the duration signal provided by the duration measuring means 183, and outputs the difference to the comparing means 186.

The threshold setting means 187 sets an appropriate ratio and/or fixed value for the signal provided by the averaging means 184, and outputs the set ratio and/or fixed value as a threshold signal to the comparing means 186.

The comparing means 186 compares the difference signal provided by the subtracting means 185 with the threshold signal provided by the threshold setting means 187, and provides the output determining means 188 with a signal representing whether the difference signal is larger or smaller than the threshold.

When the signal representing whether the difference is larger or smaller than the threshold, which is supplied by the comparing means 186, indicates that the difference is smaller, the output determining means 188 output pulses in response to the identification pulse sent from the biomedical signal identifying means 182. When the difference is larger, the output determining means 188 does not provide any output. The pulses supplied by the output determining means 188 are fed to the output means 189, and converted into a biomedical stimulation signal. Consequently, stimulation is applied to a living body via conductors or a transducer coupled to the output terminal 190.

Figure 19:
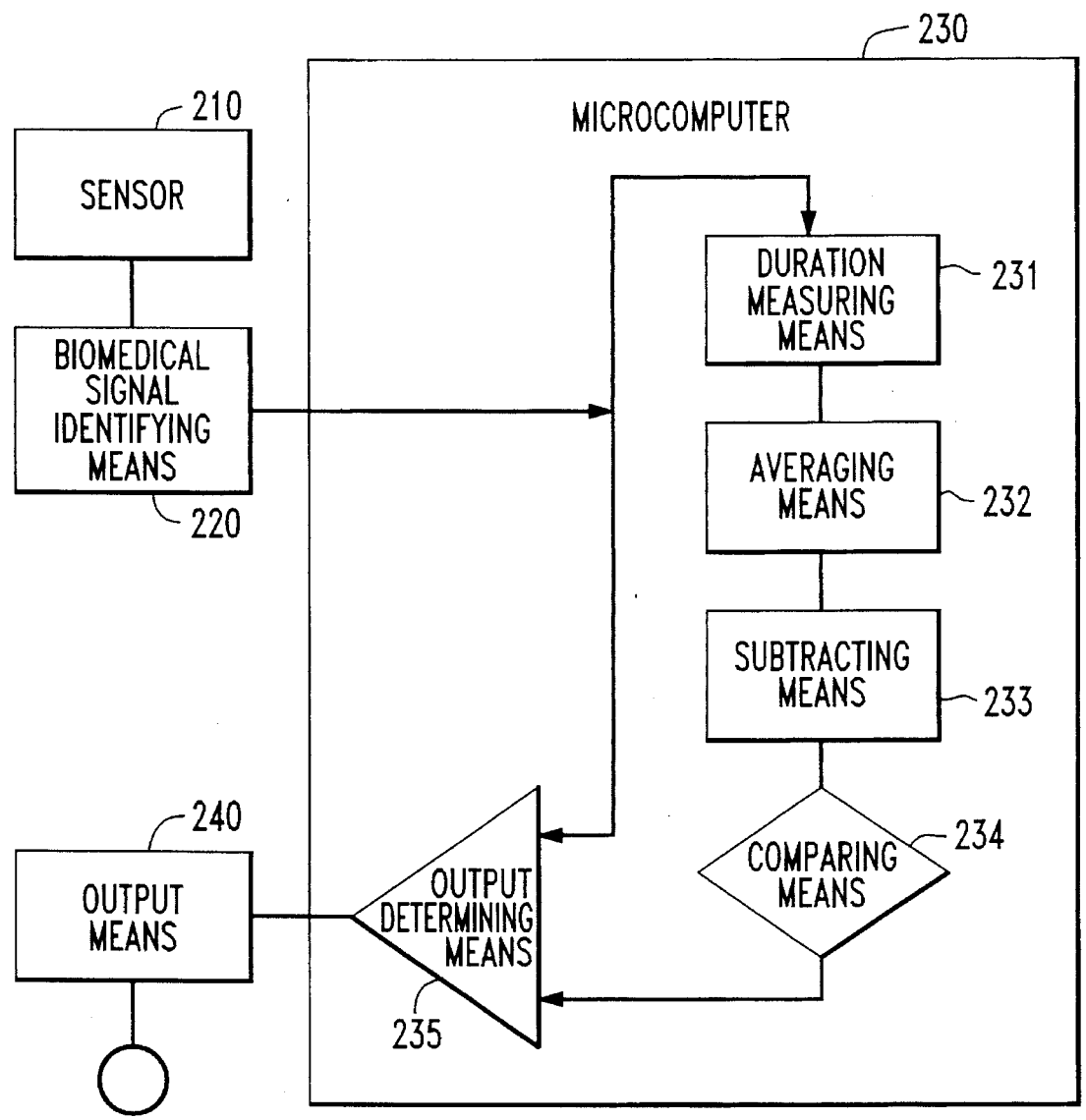
FIG. 19 is a block diagram of another example relating to the seventh aspect of the present invention.

FIG. 19 is a block diagram showing another example according to the seventh aspect of the present invention.

A sensor 210, a biomedical signal identifying means 220, and output means 240 are identical to the sensor 181, biomedical signal identifying means 182, and output means 189 in FIG. 18. The description will therefore be omitted.

230 denotes a one-chip microcomputer. 231 to 235 denotes internal components of the microcomputer 230, which determines a processing flow of the microcomputer 230. 231 denotes a duration measuring means that fetches an identification pulse from the biomedical signal identifying means 220, measures a pulse duration, and outputs a measured value A.

232 denotes an averaging means that fetches the measured value from the duration measuring means 231 multiple times, adds up and averages the multiple values, and then outputs an average value B.

233 denotes a subtracting means that executes a subtraction of A minus B, and outputs a value C.

234 denotes a comparing means. The comparing means 234 executes a comparison of C with B/N, where B/N is a threshold. To be more specific, the comparing means 234 checks if the value C provided by the subtracting means 233 is larger or smaller than a product of the average value B sent from the averaging means, and specific ratio 1/N. If the value C is larger, the comparing means 234 outputs a false signal. If the value C is smaller, the comparing means 234 outputs a true signal. 235 denotes an output determining means. With the true input sent from the comparing means 234, the output determining means 235 provides an output means 240 with an output in synchronization with a pulse supplied by the biomedical signal identifying means 220.

As mentioned above, the averaging means adds up the multiple values. The number of values must be determined in consideration of a heart rate, and may preferably be 4, 6, 8, or 16 but not limited to these numbers. The smaller the ratio set in the comparing means 234, 1/N, is, the larger the possibility that a true pulse wave may be taken for an artifact grows. The larger the ratio is, the easier the differentiation of an artifact becomes.

FIGS. 20a to 20e show waves representing the operations of the example shown in FIG. 19.

Figure 20A:
FIGS. 20a to 20e show waves detected in the components shown in the block diagram of FIG. 18 or 19.
Figure 20B:
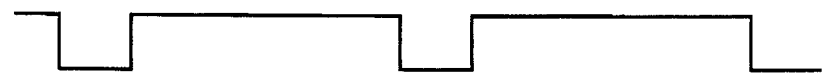

FIG. 20a represents a pulse wave detected by the pulse wave sensor shown in FIG. 19. FIG. 20b represents pulses each lasting from a rise of the pulse wave to a peak thereof, showing an example of output pulses of the biomedical signal identifying means.

Figure 20C:

FIG. 20c represents an output wave of stimulation pulses each of which is supplied during a diastolic period starting at a rise of a pulse 3B.

Figure 20D:
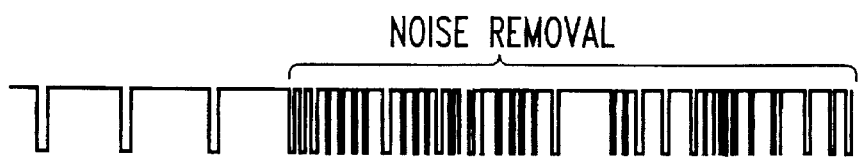
Figure 20E:
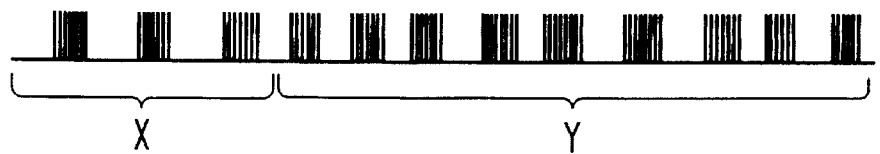

FIG. 20d and 20e in FIG. 20 show waves in which artifacts are actually mixed.

The wave of FIG. 20d is temporally-reduced wave of FIG. 20b. FIG. 20e represents a temporally-reduced wave of FIG. 20c.

During a period X, a normal pulse wave is detected and the operations are done to maintain the relationship between the waves of FIGS. 20b and 20c.

During a period Y, artifacts occur due to a swinging sensor and cause the pulse wave to have multiple peaks. Nevertheless, stimulation output pulses are supplied at certain intervals without being triggered by the artifacts.

Figure 21:
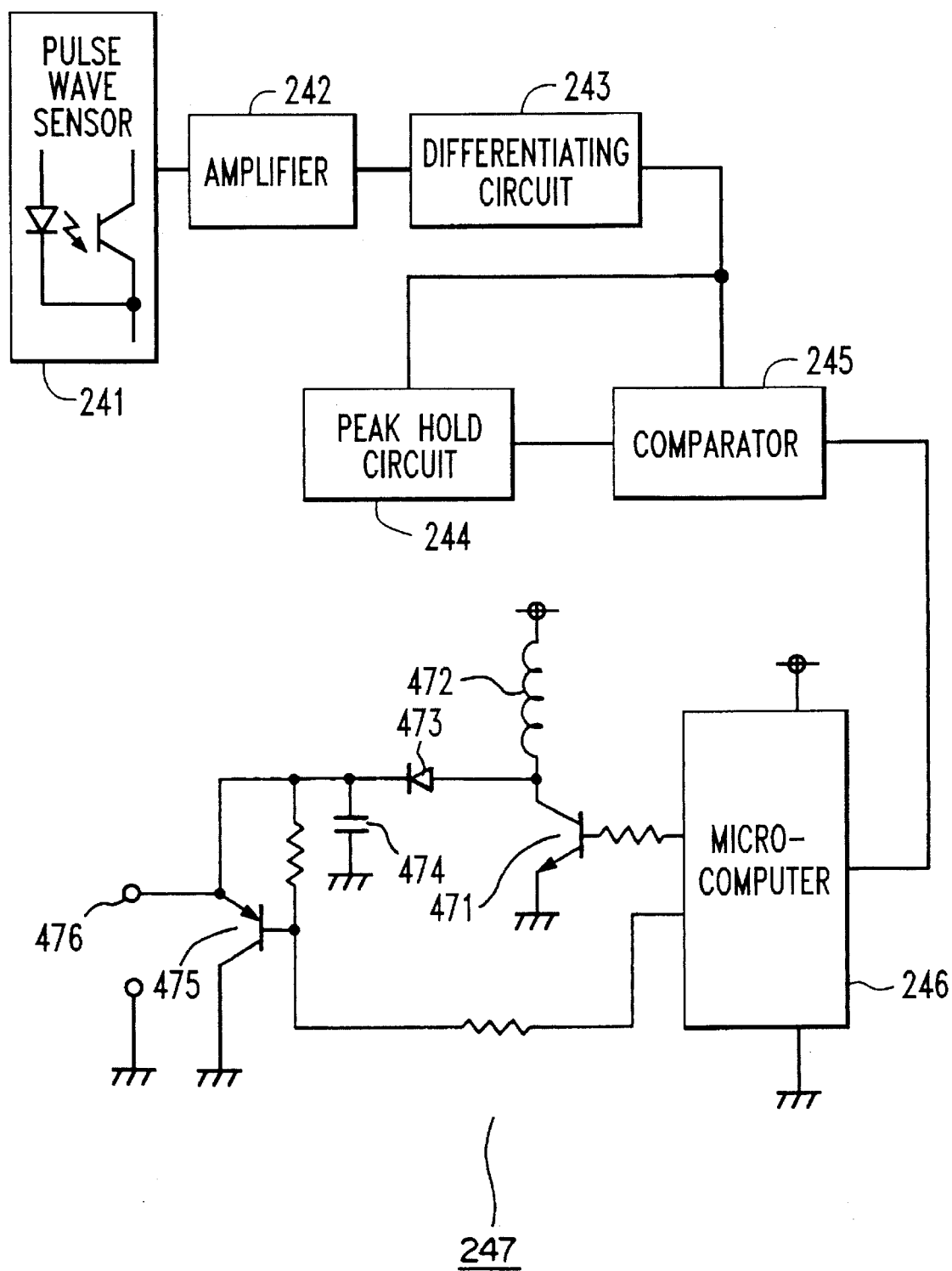
FIG. 21 is a block diagram of yet another example relating to the seventh aspect of the present invention.

FIG. 21 shows another example according to the present aspect.

241 denotes a pulse wave sensor made up of an infrared light-emitting diode and a phototransistor. The pulse wave sensor 241 is put on an earlobe, fingertip, or the like.

242 denotes an amplifier that amplifies a pulse wave electric signal detected by the pulse wave sensor.

243 denotes a differentiating circuit that converts a pulse wave signal into a differential pulse wave signal.

244 denotes a peak hold circuit that holds every leading peak of an electric signal.

245 denotes a comparator that compares an output of the amplifier with an output of the peak hold circuit. When one of the outputs exceeds the other one, a pulse is provided.

246 denotes a one-chip microcomputer in which programs are written. The programs include a program for detecting diastolic periods, a program for detecting artifacts shown in FIG. 2, and a program for outputting stimulation pulses.

247 denotes an output means that outputs stimulation pulses of several hertz at several tens of volts to several hundreds of volts. 471 denotes a switching transistor whose base is connected to the microcomputer 246, whose emitter is grounded, and whose collector is connected to each of an anode of a diode 473 and one end of a coil 472. The other end of the coil 472 is connected to a plus electrode of a power supply. The cathode of the diode 473 is connected to one terminal of a capacitor 474. 475 denotes a stimulation output transistor. The emitter of the stimulation output transistor 475 is connected to one terminal of the capacitor 474, the collector thereof is connected to an output terminal 476, and the base thereof is connected to the microcomputer 246.

Next, the operations of an example shown in FIG. 21 will be described.

A pulse wave signal detected by the pulse wave sensor 241 is amplified by the amplifier 242, and then converted into a differential wave by the differentiating circuit 243. The differential wave emerging from the differentiating circuit 243 is supplied to one terminals of the peak hold circuit 244 and comparator 245. The comparator 245 detects a rise and a fall of an output pulse which is fed to one input terminal of the comparator 245 by the differentiating circuit, and then outputs the pulse.

The microcomputer 246 inputs the output of the comparator 245, identifies a diastolic period, and detects an artifact shown in FIGS. 19 and 20. Before outputting electrical stimulation pulses, the microcomputer 246 outputs a pulse, which has a frequency ranging from several kilohertz to several tens of kilohertz, to the transistor 471. The transistor 471 puts the coil in conduction intermittently, thus causing the coil to generate boosting pulses. The boosting pulses have voltages raging from several tens of volts to several hundreds of volts. The pulse widths of the boosting pulses are, however, so narrow that the boosting pulses will not give any stimulation.

The diode 473 allows the boosting pulses induced in the coil 472 to conduct, and supplies the boosting pulses to the capacitor 474. The boosting pulses are thus stored in the capacitor 474. The microcomputer 246 outputs a pulse to the switching transistor 475 via another output terminal thereof during a diastolic period, and allows the switching transistor 475 to output stimulation pulses via the output terminal 476. The pulses have frequencies ranging from several hertz to several tens of hertz, which are supplied continuously or intermittently.

An adhesive or non-adhesive interface; such as, conductors or electrodes, is coupled with the output terminal 476. The interface is attached to the abdomen or the like of a human body.

As mentioned above, according to the seventh aspect of the present invention, artifacts can be differentiated from a normal wave, and biomedical stimulation can always be locked onto diastolic periods of a pulse wave.

Next, the eighth aspect of an electrical stimulator according to the present invention will be described. When an electrical stimulator of any of the aforesaid examples is actually put on a human body and electrical stimulation pulses are applied, only the muscles along an electrical path are put in motion. This is because however high a voltage applied is, electricity has a nature of flowing along a path permitting easy flow. Once a certain electrical path is formed, therefore, electrical stimulation pulses will not flow through other area except the formed path.

According to the eighth aspect of the present invention, an electrical stimulator comprises a pulse wave detecting means, an output unit that detects diastolic periods in a pulse wave signal provided by the pulse wave detecting means and outputs electrical stimulation during diastolic periods, a conductor for applying the electrical stimulation output of the output unit to a living body, and a belt that clamps the conductor and includes a squeezing means for squeezing the living body together with the conductor. Owing to the foregoing arrangement, electrical stimulation is applied with the abdomen pressed by the belt. A state in which electricity can easily flow will not be set up. Electrical stimulation is therefore distributed broadly. Consequently, the muscles in a broad region can be put in motion. Moreover, the blood circulation in the abdomen, in which fat is most likely to gather among all regions of a living body, is accelerated, and the muscles in a broad region are put in motion. Fat metabolism is therefore accelerated, which results in weight cutting. Furthermore, since electrical stimulation is applied only during diastolic periods (during which the veins feed blood to the heart by habit), the veins are provided with driving forces. A user will therefore not experience a fatigue resulting from remarkable improvement in acceleration of blood circulation, and can use the stimulator for a prolonged period of time. Moreover, since excess energy in the living body is consumed, appetite is halved. Thus, the requirement for weight reduction is satisfied as well. In the aforesaid examples of the present invention, an application region of a living body is the abdomen. The present invention can also be applied to the thigh, arm, or the loin.

Figure 22:
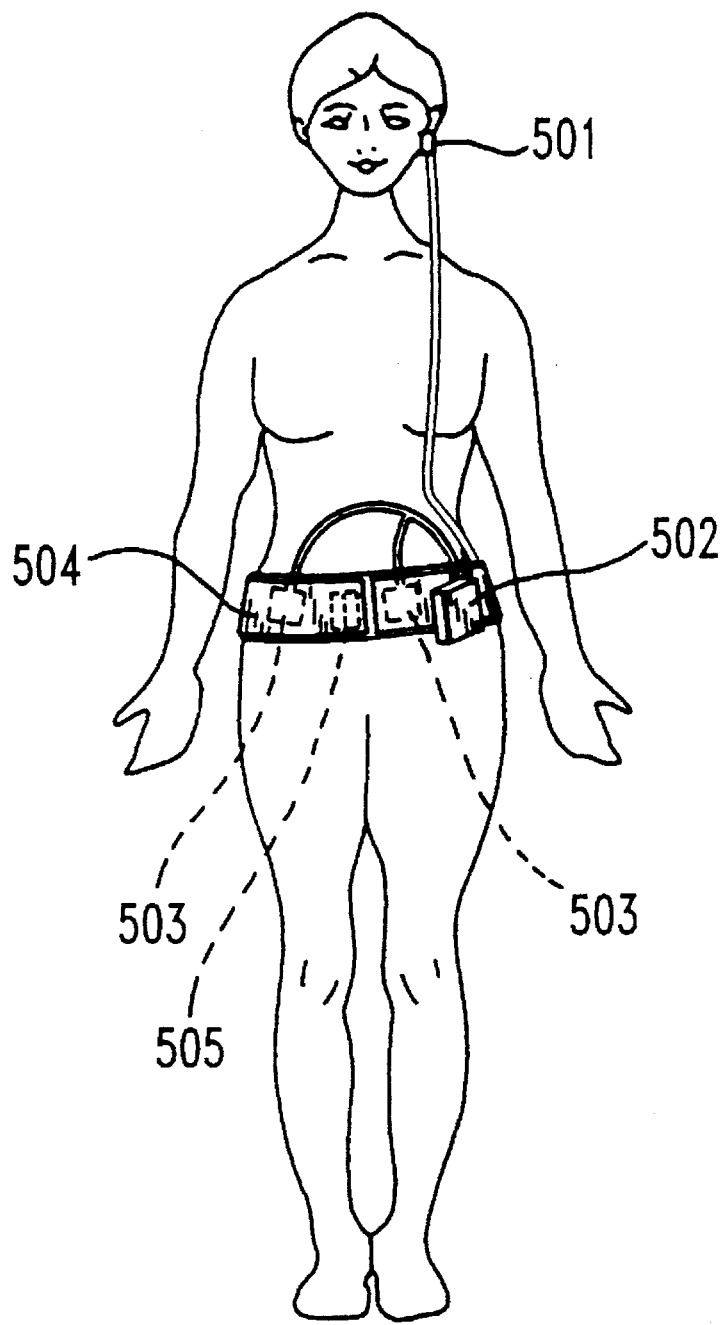
FIG. 22 shows an example of a state in which an electrical stimulator relating to the eighth aspect of the present invention is put on a human body.

FIG. 22 shows an example relating to the eighth aspect of the present invention.

501 denotes a pulse wave input means that is a sensor such as a photoelectric transducer or a piezoelectric transducer. The pulse wave input means 501 is put on an earlobe, a finger, an arm, or the like, and converts a pulse wave into an electric signal. In this example, the pulse wave input means 501 clamps an earlobe and is realized with a photoelectric transducer.

502 denotes an output unit that includes electric circuits for detecting diastolic periods in a pulse wave signal and outputting electrical stimulation pulses during the diastolic periods, and batteries for driving the electric circuits.

503 denotes a conductor made up of two conductors; a working electrode and counter electrode conductor. Each of the different and indifferent conductors has a laminated structure consisting of an adhesive conducting gel, a conducting sheet, and a non-conducting backing member. The laminated structure is presented as a mere example. Alternatively, a conducting member and a non-conducting backing member may be laminated, as long as an electrical interface is formed with respect to the abdomen of a living body.

504 denotes a belt having a squeezing means 505. The material of the belt 504 is not limited to any specific one. However, since the belt is in contact with a living body for a prolonged period of time, the belt is preferably made of a material unresponsive to a living body. The squeezing means 505 is placed on the belt 504, thus assisting the belt 504 in pressurizing the abdomen. In this example, the belt is in one piece. A planar fastener is sewn onto both ends of the belt. When the belt 504 is wound about the abdomen, the planar fasteners are joined with each other. The belt 504 pressurizes the abdomen at the joint so as to squeeze the abdomen. The squeezing means 505 in this example is the planar fasteners. Alternatively, the belt itself may be made of a stretchable raw material and shaped like a ring. In this case, the squeezing means 505 is the very belt made of a stretchable material. A pressurizing means may assume any shape and be made of any raw material, as long as it helps the belt to pressurize a living body.

The circuitry of an example of the output unit in this example is identical to the one shown in FIG. 5. The description will therefore be omitted.

In an example according to the eighth aspect, a pulse wave signal is used to detect diastolic periods, and electrical stimulation is output during the diastolic periods. Owing to a conductor for applying the electrical stimulation to a living body and a belt that clamps the conductor, brings the conductor into contact with a region of the living body, and squeezes the living body together with the conductor, blood circulation can be accelerated and weight reduction can be expected.

I claim:

1. An electrical stimulator, comprising:

a pulse wave sensor;

a differentiating means for differentiating a pulse wave electric signal provided by said pulse wave sensor;

a peak hold means for holding every peak value of a differential signal wave provided by said differentiating means;

a comparing means for comparing an output differential wave of said differentiating means with a peak hold output of said peak hold means, and outputs a pulse lasting during a period commencing when said differential wave causes a potential difference of one polarity with respect to said peak hold output and ending when a potential difference of an opposite polarity occurs between said differential wave and said peak hold output;

an electrical stimulation pulse output means for outputting electrical stimulation pulses during at least part of each of the periods set according to the output pulses of said comparing means, and for stopping the output of electrical stimulation pulses at least at the rise or fall of each of the output pulses of said comparing means.

2. An electrical stimulator according to claim 1 wherein the peak hold means comprises a circuit having a predetermined time constant for holding and decreasing the peak potential.

* * * * *